US007531182B2

(12) United States Patent
King et al.

(10) Patent No.: US 7,531,182 B2
(45) Date of Patent: May 12, 2009

(54) VACCINE AGAINST FOOT-AND-MOUTH DISEASE

(75) Inventors: Andrew Maurice Quatermain King, Pirbright Woking (GB); Alison Jane Burman, Farnham (GB); Jean-Christophe Francis Audonnet, Lyons (FR); Michel Francois Antoine Lombard, Lyons (FR)

(73) Assignee: Merial Limited, Duluth, GA (US)

( * ) Notice: Subject to any disclaimer, the term of this patent is extended or adjusted under 35 U.S.C. 154(b) by 899 days.

(21) Appl. No.: 10/327,481

(22) Filed: Dec. 20, 2002

(65) Prior Publication Data

US 2004/0001864 A1 Jan. 1, 2004

Related U.S. Application Data

(63) Continuation of application No. PCT/FR01/02042, filed on Jun. 27, 2001.

(30) Foreign Application Priority Data

Jun. 29, 2000 (FR) .................................. 00 08437

(51) Int. Cl.

*A61K 39/135* (2006.01)
*A61K 39/235* (2006.01)
*A61K 39/245* (2006.01)
*A61K 39/275* (2006.01)
*A61K 39/285* (2006.01)

(52) U.S. Cl. .................... 424/216.1; 424/199.1; 514/44

(58) Field of Classification Search ............. 424/204.1, 424/93.21; 435/456, 5, 6; 536/23.5
See application file for complete search history.

(56) References Cited

FOREIGN PATENT DOCUMENTS

WO WO 94 01133 1/1994

OTHER PUBLICATIONS

Casey et al., "Incorporation and expression of a Neo gene after transfer to caprine hematopoietic cells using a modified retrovirus,"J. Anim. Sci. 1990 68:449-453.*

Escarmis et al., "Rapid Selection in Modified BHK-21 Cells of a Foot and Mouth Disease Virus Variant Showing Alterations in Cell Tropism,"Journal of Virology, vol. 72, No. 12 (1998), pp. 10171-10179.*

STIC search results, p. 15; Nagatani et al., "Gene delivery for genetically engineered mucosal cells with enhanced function," Biotechnology Letters 22: 999-1002, 2000.*

Zurawski et al., "Definition and spatial location of mouse interleukin-2 residues that interact with its heterotrimeric receptor," The EMBO Journal, vol. 12, No. 13, pp. 5113-5119 (1993).*

Richards et al., "Liposomal Subunit Vaccines: Effects of Lipid A and Aluminum Hydroxide on Immunogenicity," Journal of Pharmaceutical Sciences vol. 85, No. 12 (1996).*

Bowie et. al., "Deciphering the Message in Protein Sequences: Tolerance to Amino Acid Substitutions," Science, vol. 247 (pp. 1306-1310).*

Beard, C. et al.: "Development of DNA Vaccines for Foot and Mouth Disease, Evaluation of Vaccines Encoding Replicating and Non-replicating Nucleic Acids in Swine", Journal of Biotechnology, NL, Elsevier Science Publishers, Amsterdam, vol. 73, No. 2-3, Aug. 20, 1999, pp. 243-249.

Abrams, Charles C. et al.: "Assembly of Foot and Mouth Disease Virus Empty Capsids Synthesized by a Vaccinia Virus Expression System", Journal of General Virology, vol. 76, No. 12; 1995, pp. 3089-3098.

Chinsangaram, Jarasvech et al.: "Antibody Response in Mice Inoculated with DNA Expressing Foot and Mouth Disease Virus Capsid Proteins", Journal of Virology, vol. 72, No. 5, Mar. 5, 1998, pp. 4454-4457.

Mayr, Gregory A. et al.: "Development of Replication-Defective Adenovirus Serotype 5 Containing the Capsid and 3C Protease Coding Regions of Foot and Mouth Disease Virus as a Vaccine Candidate". Virology, vol. 263, No. 2, Oct. 25, 1999, pp. 496-506.

Felgner, J.H. et al.: "Enhanced Gene Delivery and Mechanism Studies with a Novel Series of Cationic Lipid Formulations", Journal of Biological Chemistry, U.S. American Society of Biological Chemists, Baltimore, MD, vol. 269, No. 4, Jan. 28, 2994, pp. 2550-2561.

Cho, J.H. et al.: "Enhanced Cellular Immunity to Hepatitis C Virus Nonstructural Proteins by Codelivery of Granulocyte Macrophage-Colony Stimulating Factor Gene in Intramuscular DNA Immunization", Vaccine, GB, Butterworth Scientific Guildford, vol. 17, No. 9-10, Mar. 5, 1999, pp. 1136-1144.

* cited by examiner

*Primary Examiner*—Mary E Mosher
(74) *Attorney, Agent, or Firm*—Judy Javecki-Black; Thomas Kowalski, Esq.; Merial Limited

(57) ABSTRACT

A vaccine against foot-and-mouth disease, using as antigen an efficient amount of empty capsids of the foot-and-mouth virus. The empty capsids are obtained by expressing, in eukaryotic cells, cDNA of the P1 region of the foot-and-mouth virus genome coding for the capsid and cDNA of the region of the foot-and-mouth virus genome coding for protease 3C. The vaccine further includes a carrier or excipient pharmaceutically acceptable in veterinary medicine.

41 Claims, 4 Drawing Sheets

Thermal treatment of empty capsids modified and unmodified

Molecular weight fraction number

A. modified empty capsids of A10 foot-and-mooth virus
B. unmodified empty capsids of A10 foot-and-mooth virus

FIGURE 3(1)

```
   1 ATGGGTGCTGGGCAGTCCAGCCCAGCAACCGGCTCGCAGAACCAGTCTGGCAACACTGGCAGCA
   1▶ MetGlyAlaGlyGlnSerSerProAlaThrGlySerGlnAsnGlnSerGlyAsnThrGlySerI
  65 TAATTAACAACTACTACATGCAGCAATACCAGAACTCTATGAGCACACAGCTTGGTGACAATAC
  22▶ leIleAsnAsnTyrTyrMetGlnGlnTyrGlnAsnSerMetSerThrGlnLeuGlyAspAsnTh
 129 CATCAGTGGAGGCTCCAACGAGGGCTCCACGGACACAACTTCAACACACACAACCAACACCCAA
  43▶ rIleSerGlyGlySerAsnGluGlySerThrAspThrThrSerThrHisThrThrAsnThrGln
 193 AACAACGACTGGTTTTCAAAACTTGCCAGTTCGGCTTTTACCGGTCTGTTCGGTGCACTTCTCG
  65▶ AsnAsnAspTrpPheSerLysLeuAlaSerSerAlaPheThrGlyLeuPheGlyAlaLeuLeuA
 257 CCGACAAGAAGACGGAAGAGACTACGCTTCTGGAAGACCGCATCCTCACTACCCGCAACGGGCA
  86▶ laAspLysLysThrGluGluThrThrLeuLeuGluAspArgIleLeuThrThrArgAsnGlyHi
 321 CACCACTTCGACCACCCAGTCGAGTGTGGGAGTCACGTATGGGTACTCCACTGAGGAAGATCAC
 107▶ sThrThrSerThrThrGlnSerSerValGlyValThrTyrGlyTyrSerThrGluGluAspHis
 385 GTTGCTGGGCCCAACACATCGGGCTTAGAGACGCGGGTGGTGCAGGCAGAGAGATTTTTCAAGA
 129▶ ValAlaGlyProAsnThrSerGlyLeuGluThrArgValValGlnAlaGluArgPhePheLysL
 449 AGTTTCTGTTTGACTGGACAACGGACAAACCTTTTGGATACTTGACAAAACTGGAGCTTCCCAC
 150▶ ysPheLeuPheAspTrpThrThrAspLysProPheGlyTyrLeuThrLysLeuGluLeuProTh
 513 CGATCACCACGGTGTCTTCGGGCACCTGGTGGACTCATATGCATATATGAGGAACGGCTGGGAT
 171▶ rAspHisHisGlyValPheGlyHisLeuValAspSerTyrAlaTyrMetArgAsnGlyTrpAsp
 577 GTTGAGGTATCTGCCGTCGGCAACCAGTTCAACGGCGGGTGCCTTCTGGTGGCCATGGTGCCAG
 193▶ ValGluValSerAlaValGlyAsnGlnPheAsnGlyGlyCysLeuLeuValAlaMetValProG
 641 AGTGGAAGGCATTTGACACACGTGAAAAATACCAGCTTACCCTTTCCCACACCAGTTTATTAG
 214▶ luTrpLysAlaPheAspThrArgGluLysTyrGlnLeuThrLeuPheProHisGlnPheIleSe
 705 CCCCAGAACTAACATGACTGCCCACATCACGGTACCGTATCTTGGTGTGAACAGGTACGATCAG
 235▶ rProArgThrAsnMetThrAlaHisIleThrValProTyrLeuGlyValAsnArgTyrAspGln
 769 TACAAGAAACACAAACCTTGGACACTGGTTGTCATGGTACTATCACCCCTCACGGTCAGCAACA
 257▶ TyrLysLysHisLysProTrpThrLeuValValMetValLeuSerProLeuThrValSerAsnT
 833 CTGCCGCCCCACAAATCAAGGTCTACGCCAACATTGCCCCAACCTACGTTCACGTGGCTGGAGA
 278▶ hrAlaAlaProGlnIleLysValTyrAlaAsnIleAlaProThrTyrValHisValAlaGlyGl
 897 GCTTCCCTCGAAAGAGGGGATTTTCCCAGTTGCATGCGCAGACGGTTACGGAGGACTGGTGACA
 299▶ uLeuProSerLysGluGlyIlePheProValAlaCysAlaAspGlyTyrGlyGlyLeuValThr
 961 ACAGACCCGAAAACAGCTGACCCTGTTTACGGTAAGGTGTATAACCCGCCCAAGACCAACTACC
 321▶ ThrAspProLysThrAlaAspProValTyrGlyLysValTyrAsnProProLysThrAsnTyrP
1025 CCGGGCGCTTTACAAACCTATTGGACGTGGCCGAAGCATGTCCCACCTTTCTTCGTTTCGACGA
 342▶ roGlyArgPheThrAsnLeuLeuAspValAlaGluAlaCysProThrPheLeuArgPheAspAs
1089 TGGGAAACCGTACGTCGTTACGCGGGCAGACGACACCCGTCTTTTGGCCAAGTTTGATGTCTCC
 363▶ pGlyLysProTyrValValThrArgAlaAspAspThrArgLeuLeuAlaLysPheAspValSer
1153 CTTGCCGCAAAACACATGTCCAACACATACCTATCAGGGATTGCACAGTACTACACACAGTACT
 385▶ LeuAlaAlaLysHisMetSerAsnThrTyrLeuSerGlyIleAlaGlnTyrTyrThrGlnTyrS
1217 CTGGTACTATCAACCTGCACTTCATGTTCACAGGCTCCACTGACTCAAAAGCCCGCTACATGGT
 406▶ erGlyThrIleAsnLeuHisPheMetPheThrGlySerThrAspSerLysAlaArgTyrMetVa
1281 GGCTTACATCCCGCCTGGGGTGGAGACGCCGCCGGACACACCTGAAGAAGCTGCTCACTGCATT
 427▶ lAlaTyrIleProProGlyValGluThrProProAspThrProGluGluAlaAlaHisCysIle
1345 CACGCTGAGTGGGACACAGGACTGAACTCCAAATTCACCTTTTCAATCCCTTACGTGTCTGCCG
 449▶ HisAlaGluTrpAspThrGlyLeuAsnSerLysPheThrPheSerIleProTyrValSerAlaA
1409 CGGATTACGCGTATACCGCATCTGATACGGCAGAGACAACCAATGTACAGGGATGGGTCTGTGT
 470▶ laAspTyrAlaTyrThrAlaSerAspThrAlaGluThrThrAsnValGlnGlyTrpValCysVa
1473 TTACCAAATTACACACGGGAAGGCTGAAAATGACACCTTGTTAGTGTCGGCTAGCGCCGGCAAA
 491▶ lTyrGlnIleThrHisGlyLysAlaGluAsnAspThrLeuLeuValSerAlaSerAlaGlyLys
1537 GACTTTGAGTTGCGCCTCCCAATTGACCCCCGGACACAAACCACTACTACTGGGGAGTCCGCAG
 513▶ AspPheGluLeuArgLeuProIleAspProArgThrGlnThrThrThrThrGlyGluSerAlaA
1601 ACCCTGTCACCACCACCGTGGAGAACTACGGCGGTGATACACAAGTCCAGAGACGTCACCACAC
 534▶ spProValThrThrThrValGluAsnTyrGlyGlyAspThrGlnValGlnArgArgHisHisTh
1665 GGACGTCGGCTTCATTATGGACCGATTTGTGAAGATAAACAGCCTGAGCCCCACACATGTCATT
 555▶ rAspValGlyPheIleMetAspArgPheValLysIleAsnSerLeuSerProThrHisValIle
``` to FIGURE 3(2)

FIGURE 3(2)
from FIGURE 3(1)

```
1729  GACCTCATGCAAACCCACAAACACGGGATCGTGGGTGCGTTACTGCGTGCAGCCACGTACTACT
 577▶ AspLeuMetGlnThrHisLysHisGlyIleValGlyAlaLeuLeuArgAlaAlaThrTyrTyrP
1793  TCTCCGACTTGGAGATTGTTGTGCGGCACGATGGTAATCTGACCTGGGTGCCCAACGGTGCCCC
 598▶ heSerAspLeuGluIleValValArgHisAspGlyAsnLeuThrTrpValProAsnGlyAlaPr
1857  CGAGGCAGCCCTGTCAAACACCAGCAACCCCACTGCCTACAACAAGGCACCGTTCACGAGACTT
 619▶ oGluAlaAlaLeuSerAsnThrSerAsnProThrAlaTyrAsnLysAlaProPheThrArgLeu
1921  GCTCTCCCTTACACTGCGCCACACCGCGTGTTGGCAACTGTGTACGACGGGACAAACAAGTACT
 641▶ AlaLeuProTyrThrAlaProHisArgValLeuAlaThrValTyrAspGlyThrAsnLysTyrS
1985  CCGCAAGCGATTCGAGATCAGGCGACCTGGGGTCCATCGCGGCGCGAGTCGCGACACAACTTCC
 662▶ erAlaSerAspSerArgSerGlyAspLeuGlySerIleAlaAlaArgValAlaThrGlnLeuPr
2049  TGCTTCCTTTAACTACGGTGCAATCCAGGCACAGGCCATCCACGAGCTTCTCGTGCGCATGAAA
 683▶ oAlaSerPheAsnTyrGlyAlaIleGlnAlaGlnAlaIleHisGluLeuLeuValArgMetLys
2113  CGGGCCGAGCTCTACTGTCCCAGGCCACTTCTAGCAATAAAGGTGACTTCGCAAGACAGGTACA
 705▶ ArgAlaGluLeuTyrCysProArgProLeuLeuAlaIleLysValThrSerGlnAspArgTyrL
2177  AGCAAAAGATTATTGCGCCCGCAAAACAGCTGTTGAACTTTGACCTACTTAAGTTGGCGGGTGA
 726▶ ysGlnLysIleIleAlaProAlaLysGlnLeuLeuAsnPheAspLeuLeuLysLeuAlaGlyAs
2241  CGTTGAGTCCAACCTTGGGCCCTTCTTCTTCGCTGACGTTAGGTCAAACTTTTCGAAGCTGGTA
 747▶ pValGluSerAsnLeuGlyProPhePhePheAlaAspValArgSerAsnPheSerLysLeuVal
2305  GACACCATCAATCAGATGCAGGAGGACATGTCCACAAAACACGGACCCGACTTTAACCGGTTGG
 769▶ AspThrIleAsnGlnMetGlnGluAspMetSerThrLysHisGlyProAspPheAsnArgLeuV
2369  TGTCCGCTTTTGAGGAATTGGCCACTGGGGTTAAAGCTATCAGAACCGGTCTCGATGAGGCCAA
 790▶ alSerAlaPheGluGluLeuAlaThrGlyValLysAlaIleArgThrGlyLeuAspGluAlaLy
2433  ACCCTGGTACAAGCTCATCAAGCTCCTAAGCCGTCTGTCGTGCATGGCCGCTGTGGCAGCACGG
 811▶ sProTrpTyrLysLeuIleLysLeuLeuSerArgLeuSerCysMetAlaAlaValAlaAlaArg
2497  TCCAAGGACCCCAGTCCTTGTGGCCATCATGCTGGCCGACACCGGTCTCGAGCGTCAGAAACCTC
 833▶ SerLysAspProValLeuValAlaIleMetLeuAlaAspThrGlyLeuGluArgGlnLysProL
2561  TAAAAGTGAGAGCCAAGCTCCCACAGCAGGAGGGACCCTACGCTGGCCCGATGGAGAGACAGAA
 854▶ euLysValArgAlaLysLeuProGlnGlnGluGlyProTyrAlaGlyProMetGluArgGlnLy
2625  ACCGCTGAAAGTAAAAGTAAAAGCCCCGGTCGTTAAGGAAGGACCTTACGAGGGACCGGTGAAG
 875▶ sProLeuLysValLysValLysAlaProValValLysGluGlyProTyrGluGlyProValLys
2689  AAGCCTGTCGCTTTGAAAGTGAAAGCTAGGAACTTGATTGTCACTGAGAGTGGTGCCCCACCGA
 897▶ LysProValAlaLeuLysValLysAlaArgAsnLeuIleValThrGluSerGlyAlaProProT
2753  CCGACTTGCAGAAGATGGTCATGGGCAACACAAAGCCTGTTGAGCTTAACCTCGACGGGAAGAC
 918▶ hrAspLeuGlnLysMetValMetGlyAsnThrLysProValGluLeuAsnLeuAspGlyLysTh
2817  AGTAGCCATCTGCTGTGCTACTGGAGTGTTCGGCACTGCTTACCTCGTGCCTCGTCACCTTTTC
 939▶ rValAlaIleCysCysAlaThrGlyValPheGlyThrAlaTyrLeuValProArgHisLeuPhe
2881  GCAGAGAAGTATGACAAGATTATGTTGGACGGCAGAGCCATGACAGACAGTGATTACAGAGTGT
 961▶ AlaGluLysTyrAspLysIleMetLeuAspGlyArgAlaMetThrAspSerAspTyrArgValP
2945  TTGAGTTCGAGATTAAAGTTAAAAGGACAGGACATGCTCTCAGACGCGGCACTCATTGGTTGCT
 982▶ heGluPheGluIleLysValLysArgThrGlyHisAlaLeuArgArgGlyThrHisTrpLeuLe
3009  TCACCGTGGGAACTGCGTGAGAGACATCACGAAACACTTTCGTGATACAGCAAGAATGAAGAAA
1003▶ uHisArgGlyAsnCysValArgAspIleThrLysHisPheArgAspThrAlaArgMetLysLys
3073  GGCACCCCCGTCGTTGGTGTTGTCAACAACGCCGATGTTGGGAGACTGATTTTCTCTGGTGAGG
1025▶ GlyThrProValValGlyValValAsnAsnAlaAspValGlyArgLeuIlePheSerGlyGluA
3137  CCCTTACCTACAAGGACATTGTAGTGTGCATGGATGGAGACACCATGCCCGGCCTCTTTGCCTA
1046▶ laLeuThrTyrLysAspIleValValCysMetAspGlyAspThrMetProGlyLeuPheAlaTy
3201  CAAAGCCGCCACCAGGGCTGGCTACTGTGGAGGAGCCGTTCTTGCCAAGGACGGGGCTGACACA
1067▶ rLysAlaAlaThrArgAlaGlyTyrCysGlyGlyAlaValLeuAlaLysAspGlyAlaAspThr
3265  TTCATCGTCGGCACTCACTCTGCAGGTGGCAATGGAGTTGGATACTGCTCATGCGTTTCCAGGT
1089▶ PheIleValGlyThrHisSerAlaGlyGlyAsnGlyValGlyTyrCysSerCysValSerArgS
3329  CCATGCTTCAAAAGATGAAGGCTCACGTCGACCCTGAACCGCACCACGAGGGGTTGATTGTTGA
1110▶ erMetLeuGlnLysMetLysAlaHisValAspProGluProHisHisGluGlyLeuIleValAs
3393  TACCAGAGATGTGGAAGAGCGCGTCCACGTGATGCGCAAAACAAAGCTTTGA
1131▶ pThrArgAspValGluGluArgValHisValMetArgLysThrLysLeu•••
```

VACCINE AGAINST FOOT-AND-MOUTH DISEASE

This is a continuation of copending international application PCT/FR01/02042 having an international filing date of Jun. 27, 2001.

The present invention relates to vaccines against foot-and-mouth disease and in particular to improving their heat stability. It also relates to processes for preparing these vaccines, the use of antigens for producing these vaccines and vaccination methods using them.

It also relates in particular to nucleotide sequences, in particular cDNA, and to amino acid sequences, modified compared with natural sequences of the virus. The invention also relates to the expression products of the modified nucleotide sequences and to the foot-and-mouth antigens and virus incorporating these modifications.

Foot-and-mouth disease is one of the most virulent and contagious diseases affecting farm animals. This disease is endemic in numerous countries in the world, especially in Africa, Asia and South America. In addition, epidemic outbreaks occur from time to time.

The presence of this disease in a country may have very severe economic consequences in terms of losses of productivity, loss of weight and milk production in infected herds and in trade embargoes imposed on these countries.

The measures taken against this disease consist in strictly applying import restrictions, hygiene controls and quarantine, slaughtering sick animals and carrying out vaccination programmes using inactivated vaccines, either as a preventive measure at the national or regional level or perifocally when an epidemic outbreak occurs.

The disease is characterised by its short incubation period, its highly contagious nature, the formation of ulcers in the mouth and on the feet and sometimes the death of young animals. Foot-and-mouth disease affects a number of animal species, in particular cattle, pigs, sheep and goats.

The agent responsible for this disease is a ribonucleic acid (RNA) virus belonging to the Aphthovirus genus and the Picornaviridae family (Cooper et al., Intervirology, 1978, 10, 165-180). The foot-and-mouth disease virus is also known by the English abbreviation FMDV (foot-and-mouth disease virus). At present, 7 types of foot-and-mouth disease virus are known, the European types (A, O and C), the African types (SAT1, SAT2 and SAT3) and an Asiatic type (Asia 1). Numerous sub-types have also been distinguished (Kleid et al. in Science, 1981, 214, 1125-1129).

It is a naked icosahedral virus about 25 nm in diameter containing a single-stranded RNA molecule with a positive polarity consisting of about 8500 nucleotides. This RNA molecule is made up of a single open reading frame (ORF) which codes for a single polyprotein containing, inter alia, the capsid precursor also known as protein P1 or P88. The protein P1 is myristylated at its amino-terminal end.

During the maturation process, the protein P1 is cleaved by the protease 3C into three proteins known as VP0, VP1 and VP3 (or 1AB, 1D and 1C respectively) (Belsham G. J., Progress in Biophysics and Molecular Biology, 1993, 60, 241-261). In the virion, the protein VP0 is then cleaved into two proteins, VP4 and VP2 (or 1A and 1B respectively). The mechanism for the conversion of the proteins VP0 into VP1 and VP3 and for the formation of mature virions is not known.

The proteins VP1, VP2 and VP3 have a molecular weight of about 26,000 Da, while the protein VP4 is smaller at about 8,000 Da.

The simple combination of the capsid proteins forms the protomer or 5S molecule, which is the elementary constituent of the foot-and-mouth virus capsid. This protomer is then complexed into a pentamer to form the 12S molecule.

The virion results from the encapsidation of a genomic RNA molecule by means of the assembly of twelve 12S pentamers, thus constituting the 146S particles.

The viral capsid may also be formed without the presence of an RNA molecule inside it. The capsid is then empty. The empty capsid is also designated particle 70S. The formation of empty capsids may occur naturally during viral replication or may be produced artificially by chemical treatment.

To be effective, a vaccine against foot-and-mouth disease should generally be polyvalent. Its composition should be renewed as soon as the dominant type or types in the field change. Moreover, in order to prevent rapid development of the disease within the animal population it is advisable to have a vaccine which gives early immunity and is highly protective.

A great many hypotheses, research routes and proposals have been developed in an attempt to develop effective vaccines against foot-and-mouth disease. Currently, the only vaccines on the market are inactivated virus.

The chemical inactivation treatment may involve reducing the immunogenic power of the virus and the production of neutralising antibodies. The doses given often have to be accompanied by adjuvants for stimulating an immune response, but depending on their compositions these adjuvants may also induce inflammatory reactions. The inactivated vaccines do not confer long-term immunity, which is why booster injections have to be given every year, or more often in the event of problems, especially when epidemic outbreaks occur.

In addition, there are risks linked to incomplete inactivation and/or to the escape of virus during the production of inactivated vaccines (e.g. King et al., 1981, Nature, 293, 479-480).

The development of the techniques of genetic engineering should have made it possible to envisage the production of sub-unitary vaccines and recombinant vectors. However, in spite of numerous attempts, none has hitherto come on the market.

Prior to this work, studies have been done on natural empty capsids. In particular, Rowlands et al. (Rowlands et al., J. Gen. Virol., 1975, 26, 227-238) have shown that the virions of A10 foot-and-mouth disease comprise mainly the four proteins VP1, VP2, VP3 and VP4. By comparison, the natural empty capsids (not obtained by recombination but purified from cultures of A10 foot-and-mouth virus) essentially contain the uncleaved protein VP0; identical results with the A-Pando foot-and-mouth virus are described by Rweyemamu (Rweyemamu et al., Archives of Virology, 1979, 59, 69-79). The artificial empty capsids, obtained after dialysis in the presence of Tris-EDTA and after centrifuging, contain no protein VP4. These artificial capsids are slightly immunogenic according to Rowlands et al., and the natural empty capsids are only immunogenic after treatment with formaldehyde to stabilise them, while the antibody response induced by the natural empty capsids in the guinea-pig is nevertheless inconstant, as noted by the author. Moreover, Rowlands et al. and Rweyemamu et al. do not agree on the need to stabilise the natural empty capsids. For Rweyemamu et al., the absence of treatment with formaldehyde is not prejudicial to the level of antigenicity of the natural empty capsids. The immunogenicity is only tested by the induction of neutralising antibodies in the guinea-pig.

Some authors do not go along with this train of thought with regard to the empty capsids, or even oppose it. This is true of Doel T. R. and Chong W. K. T. (Doel et al., Archives of Virology, 1982, 73, 185-191) who conclude, from their experimental results, that the empty capsids are less immunogenic as they are less stable than the foot-and-mouth virions of sub-type A24.

The expression of the gene coding for the precursor P1 of the capsid proteins by means of a recombinant baculovirus in insect cells is compared with the expression of the gene coding for P1 associated with the protease 3C in *E. coli* (Grubman et al., Vaccine, 1993, 11, 825-829; Lewis et al., J. Virol., 1991, 65, 6572-6580). The co-expression of P1 and 3C in *E. coli* results in the assembling of empty capsids 70S. The expression product of these two constructions produces neutralising antibodies in the guinea-pig and the pig. The titres obtained with the P1/baculovirus construction are low. These same expression products induce partial protection in pigs. However, some pigs protected against the disease are not protected against the replication of the challenge virus.

The authors also find that the *E. coli* expression system does not myristylate the proteins and the protease 3C is toxic to this cell. Lewis et al. conclude that fundamental questions relating to the make-up of the virus and the structure of the capsid needed to obtain maximum protection in the animal have not been answered. Furthermore, Grubman et al. state that it would be necessary to stabilise the empty capsids before formulating the vaccine; on this point they agree about the problems encountered with the empty capsids obtained by extraction from viral cultures (see above).

The expression system consisting of the vaccinia virus has also been used to obtain empty foot-and-mouth virus capsids A10, A24 and O1K (Abrams et al., J. Gen. Virol., 1995, 76, 3089-3098). Two main constructions have been produced for each sub-type, comprising fragments of the nucleotide sequence coding for the precursor P1 and for the protease 3C either under the control of the early/late p7.5K promoter of the vaccinia virus, or of the bacteriophage T7 promoter. Only recombination and in vitro expression experiments have been carried out, on human cell cultures. The cell cultures transformed by constructions containing the p7.5K promoter have not made it possible to isolate recombinant vaccinia viruses. The reasons for this are unknown. The cell cultures transformed by the constructions containing the promoter T7 have made it possible to obtain recombinant vaccinia virus vectors, express the viral proteins VP0, VP1 and VP3 and obtain empty capsids. These experiments were intended to study the morphogenesis of foot-and-mouth virus and did not relate to the production of vaccines or any evaluation of their effectiveness.

Plasmids containing the cassette coding for P1-2A and 3C dependent on a hCMV-IE promoter have been tested by Chinsangaram et al. (Chinsangaram et al., J. Virol., 1998, 72(5), 4454-4457). Injecting these plasmids into pigs induces neutralising antibodies, and depending on the groups of animals there is no protection after 2 injections or protection is achieved after 4 injections. The authors conclude that it is advisable to improve the immune response induced by the co-expression of cytokine.

In parallel to these approaches, which have not resulted in the production of vaccines, other authors have been drawn to the use of protein VP1 of foot-and-mouth virus, on its own or in combination, or synthetic peptides.

Work with a fusion protein made up of the protein LE of the tryptophan operon of *E. coli* and a fragment of the protein VP1 of the A24 foot-and-mouth virus (amino acids 131-157 in monomer form) have been carried out in pigs (Morgan et al., Am. J. Vet. Res., 1990, 51, 40-45), comparing the results with those obtained with a similar fusion protein constructed from the A12 foot-and-mouth virus (amino acids 137-168 in tandem). Giavedoni et al. (Giavedoni et al., J. Gen. Virol., 1991, 72, 967-971) describe a fusion protein TrpE with fragments of the C terminal region of the protein VP1 of the foot-and-mouth virus O1. Huang et al. describe a recombinant fusion protein containing beta-galactosidase and two tandem repeats of VP1 sequences of the foot-and-mouth virus O (Huang et al., Viral Immunol., 1999, 12(1), 1-8).

Fusion proteins containing some or all of the protein VP1 have also been obtained by the use of viral vectors, namely a herpes virus or the vaccinia virus. CA-A-2,047,585 in particular describes a bovine herpes virus used to produce fusion proteins containing a peptide sequence of the foot-and-mouth virus (amino acids 141 to 158 of VP1 bound to amino acids 200 to 213 of VP1) fused with the glycoprotein gpIII of this bovine herpes virus.

Vaccines containing synthetic peptides based on the immunogenic regions of the protein VP1 (regarding these regions, cf. Strohmaier et al., J. Gen. Virol., 1982, 59, 295-306) have also been developed and tested.

Agterberg et al. (Vaccine, 1990, 8, 438-440) have produced, in transformed *E. coli* bacteria, a fusion protein containing two immunogenic determinants of the protein VP1 of foot-and-mouth virus A10 (regions 141-153 and 200-207) and the membrane protein PhoE of *E. coli* K-12. 100 µg of this fusion protein were then given by intramuscular route to guinea-pigs which subsequently demonstrated a detectable level of neutralising antibodies and homologous protection after challenge.

WO-A-99/66954 describes synthetic peptides corresponding to consensus sequences of VP1 antigen sites of foot-and-mouth virus of type A, O or Asia (corresponding to region 134-168 of VP1 of foot-and-mouth virus A12).

WO-A-98/12333 describes synthetic peptides containing at least 8 amino acids corresponding to a partial sequence of foot-and-mouth virus proteins.

The aim of the present invention is to provide effective and safe vaccines against foot-and-mouth disease.

The invention also sets out to provide stable anti-foot-and-mouth vaccines.

The present invention also sets out to provide anti-foot-and-mouth vaccines of this kind which are effective at low doses.

The invention thus relates to a vaccine against foot-and-mouth disease, using as antigen an effective quantity of empty capsids of the foot-and-mouth virus, these empty capsids being obtained by the expression, in eukaryotic cells, of the complementary DNA (cDNA) of the P1 region of the genome of the foot-and-mouth virus coding for the capsid and the cDNA of the region of the genome of the foot-and-mouth virus coding for the protease 3C, the vaccine further comprising a carrier or excipient which is pharmaceutically acceptable for veterinary use. By definition, no functional L protein is expressed and consequently the constructions do not contain cDNA coding for L and preferably do not contain any cDNA coding for all or part of L.

Preferably, P1 and at least part of 2A, preferably all of 2A, are expressed. The expression may also involve regions beyond 2A, and may include, for example, a part of 2B, e.g. as in the Examples.

It is preferable to express 3C and at least a part of the 3B proteins, e.g. two adjacent 3B proteins and a non-functional part of 3D, e.g. as in the Examples.

FIG. 3 gives the nucleotide sequence (SEQ ID NO: 39) and the amino acid sequence (SEQ ID NO: 38) corresponding to P1 (amino acids 2 to 737), 2A (amino acids 738 to 753), 3C (amino acids 913 to 1126) of the strain A10 of the foot-andmouth virus. The sequences of other strains of the various types and sub-types are available, notably in Genbank as mentioned in the Examples.

According to a first embodiment of the invention, the empty capsids are present in the vaccine as sub-units in an effective amount. These sub-units are preferably obtained by expression of the cDNA of regions P1 and 3C depending on a promoter, preferably the same promoter. Preferably it is an inducible promoter or a late promoter of viral origin.

The expression vectors which may be used notably comprise the viral vectors, preferably the poxviruses, notably the vaccinia virus, or the adenoviruses, the herpesviruses and the plasmid vectors, for example. These expression vectors are used to ensure in vitro expression of the empty capsids in primary eukaryotic cells or cell lines. One alternative embodiment consists in using an integration vector for integrating the expression cassette into the eukaryotic cell. The eukaryotic cells which may be used are preferably cells from cell lines, for example the cells BHK-21, CHO, COS, RK13, Vero, MDBK, PK15.

The inducible promoter may be, in particular, the bacteriophage T7 promoter, the heat-shock promoter, the metallothioneine promoter, the promoters which can be induced by ecdysone or by steroids. When the bacteriophage T7 promoter is used, the polymerase of bacteriophage T7 and the empty capsids are co-expressed.

The late promoter of viral origin may be, in particular, when a poxvirus is used as vector, the promoter P11K of the vaccinia virus, P28K of the vaccinia virus, P160K ATI of the cowpox virus.

The sub-units are preferably preserved and stored by freezing or lyophilisation.

The doses administered may notably be between 0.3 and 30 µg, notably between 0.5 and 20 µg, preferably between 1 and 10 µg and even more preferably between 1 and 5 µg, per dose.

The dosage volumes may preferably be between 0.2 and 5 ml, preferably between 1 and 3 ml.

The uptake medium (excipient, carrier) for the sub-unit vaccines is preferably a medium which allows conservation of the empty capsids, e.g. of the DMEM type.

The sub-unit vaccine may be administered notably by parenteral route, preferably by subcutaneous or intramuscular route, or by intradermal route, notably using a needle-less device (pressurised jet).

The man skilled in the art has the necessary competence to define precisely the number of injections and the doses of each vaccine to be used for each vaccination programme.

These vaccines preferably comprise one or more adjuvants.

As adjuvants for the sub-unit vaccines according to the invention, adjuvant may be, in particular, (1) aluminium hydroxide, saponine (for example QuilA), avridine, DDA, (2) an acrylic or methacrylic acid polymer, a polymer of maleic anhydride and alkenyl derivative, or (3) the vaccine may be made in the form of a water-in-oil, oil-in-water or water-in-oil-in-water emulsion.

The emulsion may be based notably on light liquid paraffin oil (of the European Pharmacopoeia type); isoprenoid oil such as squalane or squalene; oil resulting from the oligomerisation of alkenes, particularly isobutene or decene; esters of acids or alcohols with a linear alkyl group, more particularly the vegetable oils, ethyl oleate, propylene glycol di(caprylate/caprate), glycerol tri(caprylate/caprate), propylene glycol dioleate; esters of branched fatty acids or alcohols, in particular esters of isostearic acid. The oil is used together with emulsifiers to form the emulsion. The emulsifiers are preferably non-ionic surfactants, in particular the polyoxyethylenated fatty acids (e.g. oleic acid), the esters of sorbitan, of mannide (e.g. anhydromannitol oleate), of glycerol, of polyglycerol, of propylene glycol and of optionally ethoxylated oleic, isostearic, ricinoleic, hydroxystearic acid, the ethers of fatty alcohols and polyols (e.g. oleic alcohol), the polyoxypropylene-polyoxyethylene block copolymers, in particular Pluronic®, notably L121 (cf. Hunter et al., 1995, "The Theory and Practical Application of Adjuvants" (Ed. Steward-Tull, D.E.S.) John Wiley and Sons, N.Y., 51-94; Todd et al., Vaccine, 1997, 15, 564-570).

The polymers of acrylic or methacrylic acid are crosslinked particularly by polyalkenyl ethers of sugars or polyalcohols. These compounds are known by the name carbomer (Pharmeuropa vol. 8, n° 2, June 1996). The skilled person may also refer to U.S. Pat. No. 2,909,462 (incorporated by reference) which describes acrylic polymers of this kind crosslinked by a polyhydroxyl compound having at least 3 hydroxyl groups, preferably not more than 8, the hydrogen atoms of at least three hydroxyls being replaced by unsaturated aliphatic radicals having at least 2 carbon atoms. The preferred radicals are those containing 2 to 4 carbon atoms, e.g. vinyls, allyls and other ethylenically unsaturated groups. The unsaturated radicals may themselves contain other substituents such as methyl. The products sold under the name Carbopol® (BF Goodrich, Ohio, USA) are particularly suitable. They are crosslinked by an allyl saccharose or by allylpentaerythritol. Of them, mention may be made of Carbopol® 974P, 934P and 971 P.

Of the copolymers of maleic anhydride and an alkenyl derivative, the preferred ones are EMA® (Monsanto) which are linear or crosslinked copolymers of maleic anhydride and of ethylene, crosslinked by divinylether for example. Reference may be made to J. Fields et al., Nature, 186: 778-780, 4th June 1960 (incorporated by reference).

In terms of their structure, the polymers of acrylic or methacrylic acid and EMA® are preferably formed from basic motifs of the following formula:

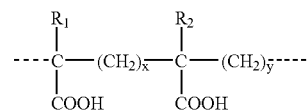

wherein:
R1 and R2, which may be identical or different, represent H or CH3
x=0 or 1, preferably x=1
y=1 or 2, with x+y=2

For the EMA®, x=0 and y=2. For the carbomers, x=y=1.

The polymer concentration in the final vaccine composition will be from 0.01% to 1.5% P/V, more particularly from 0.05 to 1% P/V, preferably from 0.1 to 0.4% P/V.

According to a second embodiment of the invention, the vaccine contains an expression vector containing the cDNA so as to produce the empty capsids in vivo. These empty capsids are preferably obtained in vivo by expression of the cDNA of the P1 and 3C regions inserted in a plasmid expression vector or in a viral expression vector and made dependent on a promoter, preferably the same promoter. The promoter is preferably a strong early promoter or a late promoter of viral origin.

In the case of viral vectors a late promoter of viral origin is preferably used.

The viral vectors are preferably poxviruses, notably the vaccinia virus, avipox (e.g. fowipox, canarypox), racoonpox, swinepox, capripox, or the replicatory adenoviruses, notably porcine adenovirus, and herpesviruses. The late promoter of viral origin may be, in particular, for the poxviruses, the P11K promoter of the vaccinia virus, P28K of the vaccinia virus, P160K ATI of the cowpox virus.

By definition, a plasmid expression vector (or plasmid) covers a DNA transcription unit comprising a polynucleotide sequence containing the cDNA which is to be expressed and the elements necessary for its expression in vivo. The circular, super-coiled or uncoiled plasmid form is preferred. The linear form also comes under the scope of this invention.

In the case of plasmids a strong early promoter of viral origin or of cellular origin is preferably used and in particular the early promoter of the cytomegalovirus CMV-IE, of human or murine origin, or possibly of some other origin such as rat or guinea-pig. It is also possible to use the early or the late promoter of the SV40 virus or the LTR promoter of the Rous sarcoma virus. The cellular promoter may be the promoter of a cytoskeleton gene, such as for example the desmine promoter, or the actin promoter.

The recombinant vaccines are preferably preserved and stored by freezing or lyophilisation or in liquid form.

The uptake medium (excipient, carrier) is preferably a 0.9% NaCl saline solution or a phosphate buffer.

The quantity of viral vectors used in the vaccine according to the present invention is at least about $10^3$ pfu. It is preferably between about $10^4$ pfu and about $10^{10}$ pfu, e.g. about $10^5$ pfu and $10^9$ pfu, more particularly between about $10^6$ pfu and about $10^8$ pfu, per dose.

The quantity of plasmid vectors used in the vaccines according to the present invention is between about 1 μg and about 2 μg, and preferably between about 50 μg and about 1 mg, per dose.

The dosage volumes may preferably be between 0.2 and 5 ml, preferably between 1 and 3 ml.

The recombinant vaccines according to the invention may be administered by the usual administration routes using known methods. According to a preferred embodiment of the invention, they are administered by intramuscular or subcutaneous route or using a needle-less injector by intradermal route. In particular for the viral vectors, the intramuscular or subcutaneous route is preferred. For viral or plasmid vectors the mucosal route may also be used (e.g. oral, nasal).

Preferably, these vaccines comprise one or more adjuvants. For the viral vectors it is advantageous to use a polymer of acrylic or methacrylic acid, or a polymer of maleic anhydride and an alkenyl derivative, and in particular the carbomers, notably Carbopol® (these adjuvants are described hereinbefore).

For the plasmid vectors, it is advantageous to formulate them by adding, as adjuvant, cationic lipids containing a quaternary ammonium salt, of formula:

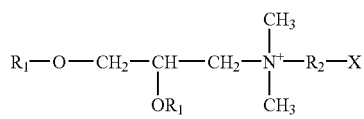

wherein R1 is a linear, saturated or unsaturated, aliphatic radical having 12 to 18 carbon atoms, R2 is another aliphatic radical containing 2 or 3 carbon atoms, and X is a hydroxyl or amino group.

Preferably it is DMRIE (N-(2-hydroxyethyl)-N,N-dimethyl-2,3-bis(tetradecyloxy)-1-propanammonium; WO-A-9634109), preferably combined with a neutral lipid, notably DOPE (dioleoyl-phosphatidyl-ethanolamine; Behr J. P., 1994, Bioconjugate Chemistry, 5, 382-389) to form DMRIE-DOPE. Preferably, the plasmid is mixed with this adjuvant in advance and before it is given to the animal the mixture thus formed is given time to complex, e.g. for a period ranging from 10 to 60 minutes, notably of the order of 30 minutes.

When DOPE is present, the molar ratio of DMRIE:DOPE preferably ranges from 95:5 to 5:95, and is more particularly 1:1.

The weight ratio of plasmid:adjuvant, notably DMRIE or DMRIE-DOPE may range in particular from 50:1 to 1:10, in particular from 10:1 to 1:5, and preferably from 1:1 to 1:2.

The vaccines according to the invention, with or without adjuvants as described above, may also contain as adjuvants one or more cytokines, which are added or expressed in vivo. Preferably, GM-CSF is used (in English: Granulocyte Macrophage Colony Stimulating Factor: Clark S.C. et al. Science 1987. 230. 1229; Grant S. M. et al. Drugs 1992. 53. 516), which may be done by incorporating GM-CSF protein directly into the vaccine composition or preferably par inserting the nucleotide sequence coding for GM-CSF in an expression vector under conditions which allow its expression in vivo, e.g. the vector containing the nucleotide sequence coding for the FMDV antigen or another vector. A plasmid is preferably used as the expression vector. The choice of the GM-CSF is preferably made as a function of the animal species to be vaccinated; thus, for cattle, bovine GM-CSF (cf. e.g. Maliszewski et al. Molec. Immunol. 1988. 25. 843-850) is used; for pigs, porcine GM-CSF is used (cf. e.g. Inumaru S. and Takamatsu H., Immunol. Cell. Biol. 1995.75. 474-476).

For the production of vectors expressing GM-CSF, the GM-CSF sequences are available in Genbank, D21074 for pigs, U22385 for cattle and X55991 for sheep.

The present invention also relates to a process for preparing a sub-unit anti-foot-and-mouth vaccine in which empty capsids of this virus are produced by expression of the cDNA of the region P1 and by expression of the cDNA of the region 3C, and it is formulated in a carrier or excipient which is suitable for veterinary use, preferably in the presence of at least one adjuvant.

The invention also relates to the use of empty capsids produced in vitro according to the invention, for the preparation of a sub-unit anti-foot-and-mouth vaccine, further comprising a carrier or excipient which is suitable for veterinary use, preferably in the presence of at least one adjuvant.

The invention also relates to a method of vaccinating against foot-and-mouth disease, comprising administering to the animal, particularly a farm animal, in particular bovine, ovine, porcine or caprine species, a sub-unit vaccine according to the invention. Methods of administration and doses are defined hereinbefore.

The various features described above with regard to the sub-unit vaccine according to the invention apply to these different objects.

The present invention also relates to a process for preparing a recombinant anti-foot-and-mouth vaccine in which viral or plasmid vectors are produced which express protein P1 and protein 3C in vivo under conditions leading to the formation of empty capsids, and these vectors are formulated in a carrier or excipient suitable for veterinary use, preferably in the presence of at least one adjuvant.

The invention also relates to the use of viral or plasmid vectors according to the invention, for the preparation of a recombinant anti-foot-and-mouth vaccine, further comprising a carrier or excipient suitable for veterinary use, preferably in the presence of at least one adjuvant.

The invention also relates to a method of vaccinating against foot-and-mouth disease, comprising administering to the animal, particularly a farm animal, in particular bovine, ovine, porcine or caprine species, a recombinant vaccine according to the invention. Methods of administration and doses are defined herein before.

The various characteristics described above regarding the vaccines which use viral or plasmid vectors according to the invention also apply to these different objects.

The invention also relates to a multivalent vaccine or a combination of vaccines containing a vaccine according to the invention, and at least one other vaccine against a foot-and-mouth virus of another type (e.g. O, A, C, SAT1, SAT2, SAT3, Asia), of another sub-type (e.g. A10, A12, A24, O1) or of another variant, preferably according to the invention, in a carrier or excipient suitable for veterinary use and preferably with an adjuvant, notably one of those described above.

The invention also relates to a multivalent vaccine or a combination of vaccines containing a vaccine according to the invention, and at least one vaccine against another pathogen, notably the rabies virus, in a carrier or excipient suitable for veterinary use and preferably with an adjuvant, notably one of those described above.

The invention also relates to improving the temperature stability of the empty foot-and-mouth virus capsids and the vaccines obtained. The temperature stability of the empty capsids is advantageously ensured by the formation of disulphide bridges.

In particular, this improvement is obtained by replacing an amino acid of the original sequence with a cysteine amino acid in the polypeptide sequence of a structural protein of the capsid, the protein VP2, this amino acid being in position 179 on the amino acids sequence SEQ ID NO 38 (FIG. 3). As a general rule, the position of this amino acid is identical in the other foot-and-mouth viruses (as is the case particularly with the strains described in the examples). In the sequences to other viruses, the position may possibly be very slightly different and may be 178 or 180, for example. The region containing this amino acid corresponds to an alpha helix. To identify or confirm the amino acid which is to be mutated, the amino acid sequences of this region are aligned with the corresponding region (for example of the order of about ten or slightly more—e.g. 10 to 20—amino acids) on the sequence SEQ ID NO 38, taking account of the fact that the sequences are well conserved in structure among the different foot-and-mouth viruses. It was found, in particular, by comparing the sequences of the strains O1, A10, A24, A22, C1, C3, SAT2, that the region may be written as follows:

X1 Gly X3 X4 Gly X6 Leu X8 X9 Ser X11 X12 Tyr Met (SEQ ID NO: 42)

where

X4 and X11 are Tyr, His or Phe (hydrophobic amino acids)

X3, X8 and X12 are Val, Met, Ile, Thr or Ala

X6 is His, Gln, Arg, Lys, Ser or Gly; this is the amino acid to mutate into Cys

X1 is His or Lys (basic amino acids)

X9 is Asp, Glu or Lys (acidic and basic amino acids).

The amino acid to mutate is the histidine located in position 179 of the P1 precursor of the foot-and-mouth virus A10.

This is the serine in position 179 of the P1 precursor of the foot-and-mouth virus O1.

This is the glycine in position 179 of the P1 precursor of the foot-and-mouth virus C1.

This is the histidine in position 179 of the precursor P1 of the foot-and-mouth virus A24.

By convention, the methionine corresponding to the initiation codon (which is not present in the natural sequence and is therefore added) is numbered 1.

At the nucleotide level, this comes to replace the codons of origin by a codon coding for cysteine, either a TGT or TGC codon for the cDNA, or UGU or UGC for the RNA.

The present invention thus also relates to the nucleotide sequences, notably the cDNA incorporating this modification. In particular, the invention relates to the sequences cDNA, and the vectors incorporating them, comprising the sequence coding for VP2 (or VP0), and more particularly for P1, which incorporate this modification, for example cDNA sequences coding for P1-2A or P1-2A-part of 2B, and the sequences incorporating them, for example sequences incorporating them with the sequences allowing their expression (promoter, ATG codon, etc.).

The present invention also relates to the amino acid sequences, obtained from these nucleotide sequences, as well as the empty capsids and the heat-stable foot-and-mouth viruses (i.e. having improved thermal stability). Preferably, they comprise disulphide bridges which are not presents in the natural capsids and viruses. In particular, they comprise VP2 proteins containing a cysteine instead of a natural amino acid, as described above.

According to the preferred embodiment of the invention, the vaccines described above are based on the use of this modification and hence the cDNA sequences are modified in consequence and the empty capsids obtained either in vitro or in vivo have the disulphide bridges.

Similarly, all the other objects (methods, use, processes) of the invention described above may and preferably do have these features.

BRIEF DESCRIPTION OF THE DRAWINGS

The invention will now be described in more detail by means of embodiments as non-restrictive examples, and referring to the drawings in which

FIG. 3: nucleotide sequence and amino acid sequence corresponding to P1 (amino acids 2 to 737), 2A (amino acids 738 to 753), 3C (amino acids 913 to 1126) of the A10 strain of foot-and-mouth virus List of sequences SEQ ID for the constructions of the present invention SEQ ID NO 1: oligonucleotide JCA305

SEQ ID NO 2: oligonucleotide JCA306

SEQ ID NO 3: oligonucleotide JCA307

SEQ ID NO 4: oligonucleotide JCA308

SEQ ID NO 5: oligonucleotide JCA309

SEQ ID NO 6: oligonucleotide JCA310

SEQ ID NO 7: oligonucleotide JCA311

SEQ ID NO 8: oligonucleotide JCA312

SEQ ID NO 9: oligonucleotide JCA313

-continued

SEQ ID NO 10: oligonucleotide JCA314

SEQ ID NO 11: oligonucleotide JCA315

SEQ ID NO 12: oligonucleotide JCA316

SEQ ID NO 13: oligonucleotide JCA317

SEQ ID NO 14: oligonucleotide JCA318

SEQ ID NO 15: oligonucleotide JCA319

SEQ ID NO 16: oligonucleotide JCA320

SEQ ID NO 17: oligonucleotide JCA321

SEQ ID NO 18: oligonucleotide JCA322

SEQ ID NO 19: oligonucleotide JCA323

SEQ ID NO 20: oligonucleotide JCA324

SEQ ID NO 21: oligonucleotide JCA325

SEQ ID NO 22: oligonucleotide JCA326

SEQ ID NO 23: oligonucleotide JCA327

SEQ ID NO 24: oligonucleotide JCA328

SEQ ID NO 25: oligonucleotide JCA329

SEQ ID NO 26: oligonucleotide JCA330

SEQ ID NO 27: oligonucleotide JCA331

SEQ ID NO 28: oligonucleotide JCA332

SEQ ID NO 29: oligonucleotide JCA333

SEQ ID NO 30: oligonucleotide JCA334

SEQ ID NO 31: oligonucleotide JCA335

SEQ ID NO 32: oligonucleotide JCA336

SEQ ID NO 33: oligonucleotide JCA337

SEQ ID NO 34: oligonucleotide JCA338

SEQ ID NO 35: oligonucleotide JCA339

SEQ ID NO 36: oligonucleotide JCA340

SEQ ID NO 37: oligonucleotide JCA341

Figure 1:
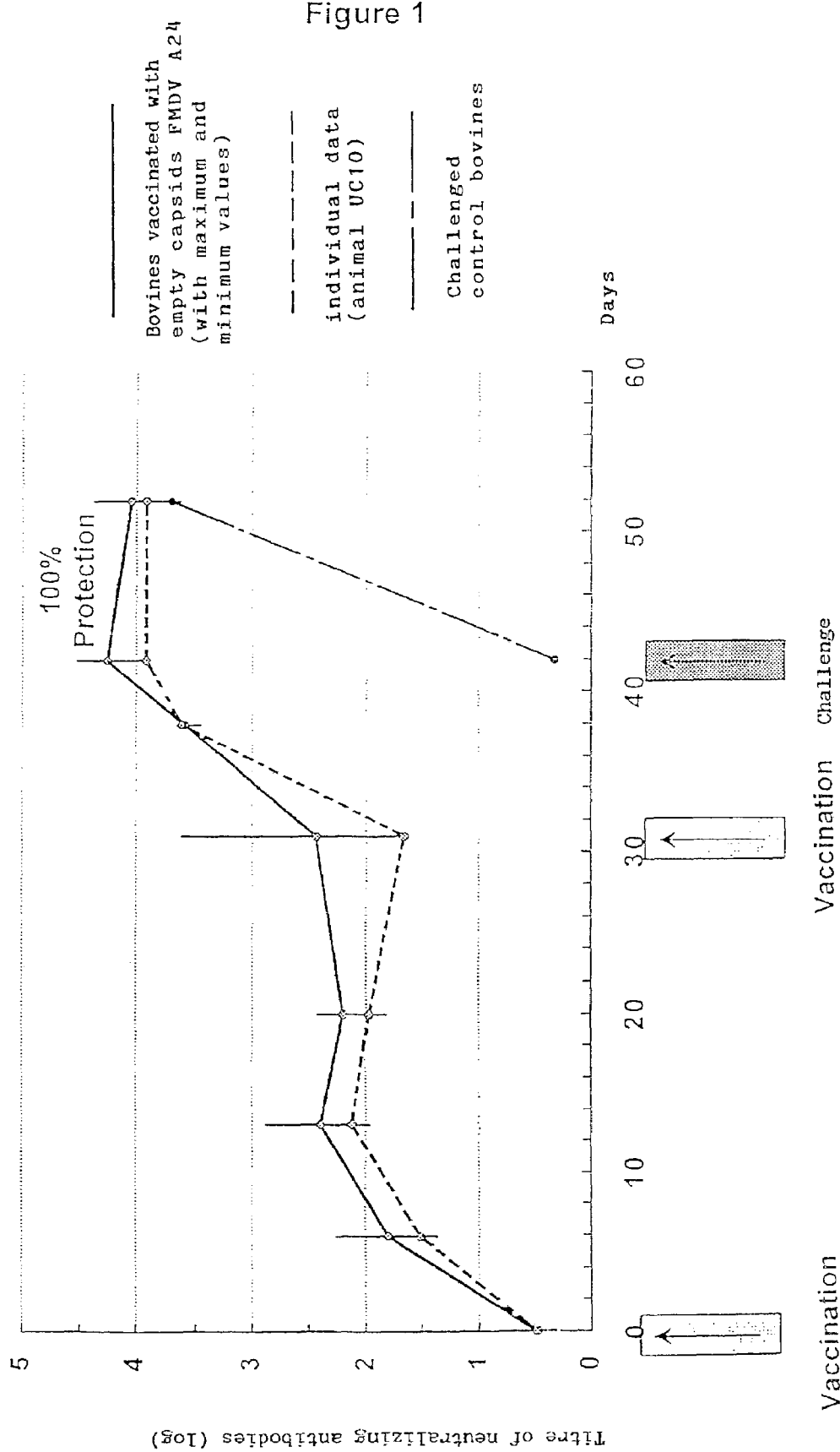
FIG. 1: graph of the titres of anti-foot-and-mouth A24 neutralising antibodies measured in cattle (expressed as log)

SEQ ID NO 38: amino acid sequence corresponding to P1 (amino acids 2 to 737), 2A (amino acids 738 to 753), 3C (amino acids 913 to 1126) of the foot-and-mouth virus A10.

SEQ ID NO 39: nucleotide sequence corresponding to P1, 2A, 3C of the foot-and-mouth virus A10.

SEQ ID NO 40: oligonucleotide JCA342

SEQ ID NO 41: oligonucleotide JCA343

EXAMPLES

All the constructions are produced using the standard techniques of molecular biology (cloning, digestion with restriction enzymes, synthesis of a single-stranded complementary DNA, polymerase chain reaction, extension of an oligonucleotide by DNA polymerase . . . ) described by Sambrook J. et al. (Molecular Cloning: A Laboratory Manual. 2nd Edition. Cold Spring Harbor Laboratory. Cold Spring Harbor. New York. 1989). All the restriction fragments used for the present invention, as well as the various fragments of polymerase chain reaction (PCR), are isolated and purified using the "Geneclean®" kit (BIO101 Inc. La Jolla, Calif.).

Nucleotide and polypeptide sequences of foot-and-mouth disease virus can be obtained from the GenBank database, notably under nos. X00429 for A10, X00871 for O1K, AJ251476 for A24, and AJ133357 for C Spain Olot.

Example 1

Culture of Strains of Foot-and-Mouth Virus

To amplify them, the strains of foot-and-mouth virus designated O1K (Forss et al., 1984, Nucleic Acids Res., 12(16), 6587-6601), A24 (Weddell et al., 1985, Proc. Natl. Acad. Sci. USA, 82, 2618-2622), A10 (Carroll et al., 1984, Nucleic Acids Res., 12(5), 2461-2472), C Spain Olot (Toja et al., 1999, Virus Res., 64(2), 161-171) are cultivated on BHK-21 cells (Baby Hamster Kidney, obtainable from the American Type Culture Collection (ATCC) under number CCL-10).

The cells BHK-21 are cultured in Falcon 25 cm2 with MEM Eagle medium supplemented with 1% of yeast extracts and 5% calf serum containing about 100,000 cells per ml. The cells are cultivated at +37° C.

After 3 days the layer of cells reaches confluence. The culture medium is then replaced with MEM Eagle medium without serum but supplemented with 0.4% of lactalbumin hydrolysate and 0.3% peptone (pH 7.4) and the foot-and-mouth virus is added in an amount of 1 pfu to about 20 cells.

When the cytopathogenic effect (CPE) is complete (generally 24 hours after the start of culturing), the viral suspensions are harvested, then clarified by centrifuging and frozen at −70° C. 3 to 4 successive runs are generally needed to produce one batch of virus. The batch of virus is stored at −70° C.

These operations are repeated for each strain of foot-and-mouth virus.

Example 2

Extraction of the Viral RNA from the Foot-and-Mouth Virus Strains

The viral RNA contained in 100 ml of viral suspension of the strain of foot-and-mouth virus A24, obtained in Example 1, is extracted after freezing with the solutions of the <<High PureTM Viral RNA Kit>> Cat # 1 858 882, Roche Molecular Biochemicals), following the manufacturer's instructions for the extraction steps. The RNA residue obtained at the end of the extraction is resuspended with 10 ml of sterile distilled water without RNase.

The viral RNA of each of the strains of foot-and-mouth virus is extracted under the same conditions.

Example 3

Construction of the Expression Plasmid for the Empty Capsids of the Foot-and-Mouth Virus A10

The complementary DNA (cDNA) of the foot-and-mouth virus A10 is synthesised with the <<Gene Amp RNA PCR Kit>> (Cat# N 808 0017, Perkin-Elmer, Norwalk, Conn. 06859, USA) under the conditions specified by the supplier. For the first fragment, a reverse transcription reaction, followed by a chain reaction of amplification ("TI-ACP" or "RT-PCR" reaction) is carried out with 50 µl of the viral RNA suspension of the foot-and-mouth virus A10 (Example 2) and with the following oligonucleotides:

```
JCA305 (37 mer)  5'TTTTGATATCATGGGTGCTGGGCAGTCCAGCCCAGCA 3'    (SEQ ID NO 1)
and JCA306 (21 mer)  5'TTCACGACGAAAGTACTATCC 3'.                    (SEQ ID NO 2)
```

This pair of oligonucleotides enables an EcoRV restriction site and an ATG phase initiating codon to be incorporated in the nucleotide sequence coding for P1.

The first strand of cDNA is synthesised by extending the oligonucleotide JCA306, after hybridisation of the latter with the RNA matrix.

The conditions of synthesis of the first strand of cDNA are a temperature of 42° C. for 15 min, then 99° C. for 5 min, and finally 4° C. for 5 min. The conditions of the PCR reaction in the presence of the pair of oligonucleotides JCA305 and JCA306 are a temperature of 95° C. for 2 min, then 35 cycles (95° C. for 1 min, then 62° C. for 1 min, and 72° C. for 2 min), and finally 72° C. for 7 min to produce a 2583 bp fragment.

This fragment is digested with EcoRV then with XhoI to isolate the fragment EcoRV-XhoI of about 2550 bp, after agarose gel electrophoresis. This fragment is called fragment A.

For the second fragment, a PCR reaction is carried out with 50 μl of the viral RNA suspension of the foot-and-mouth virus A10 (Example 2) and with the following oligonucleotides:

```
JCA307 (21 mer)                    (SEQ ID NO 3)
5' CTGAAGGACCCTACTCCGGGC 3'
and JCA308 (37 mer)                    (SEQ ID NO 4)

5' TTTTAGATCTTCAAAGCTTTGTTTTGCGCATCACGTG 3'.
```

This pair of oligonucleotides allows a BglII restriction site and a phase stop codon to be incorporated with the nucleotide sequence coding for the protease 3C.

The first strand of cDNA is synthesised by elongating the oligonucleotide JCA308, after hybridisation of the latter with the RNA matrix.

The conditions of synthesis of the first strand of cDNA are a temperature of 42° C. for 15 min, then 99° C. for 5 min, and finally 4° C. for 5 min. The conditions of the PCR reaction in the presence of the pair of oligonucleotides JCA307 and JCA308 are a temperature of 95° C. for 2 min, then 35 cycles (95° C. for 1 min, then 62° C. for 1 min, and 72° C. for 2 min), and finally 72° C. for 7 min to produce a 936 bp fragment.

This fragment is digested with BglII then with XhoI to isolate the fragment BglII-XhoI of about 900 bp, after agarose gel electrophoresis. This fragment is called fragment B.

Fragment A and fragment B are ligated with the expression plasmid pVR1012 (Hartikka J. et al., 1997, Human Gene Therapy, 7, 1205-1217), previously digested with BglII and EcoRV, to give the plasmid pJCA161 (8327 bp). This plasmid contains, under the control of the early promoter of the human cytomegalovirus or hCMV-IE (Immediate Early human Cytomegalovirus), an insert coding for the part of the polyprotein sufficient to generate capsid proteins capable of self-assembly.

Example 4

Construction of the Expression Plasmids for the Empty Capsids of the Foot-and-Mouth Virus of Sub-types O1K, C Spain Olot and A24

The cDNA of the foot-and-mouth viruses of sub-types O1K, C Spain Olot and A24 are synthesised as described in Example 3.

For O1K, the oligonucleotide pair:

```
JCA309 (37 mer)  5'TTTTGATATCATGGGGGCTGGACAATCCAGTCCAGCG   (SEQ ID NO 5)
                 3'
and JCA310 (21 mer)  5'TTCACGACGAAGGTGCTGTCC 3'                 (SEQ ID NO 6)
``` is used during the first PCR reaction to produce a fragment of 2583 base pairs (bp), then after digestion and isolation an EcoRV-XhoI fragment of about 2550 bp. This fragment is called fragment C.

During the second PCR reaction, the oligonucleotide pair:

```
JCA311 (18 mer)  5'AAGGACCCTACGCCGGAC 3'                     (SEQ ID NO 7)
and JCA312 (34 mer)  5'TTTTAGATCTTCAAAGCTTGGTTTTGCGCATCAC 3'   (SEQ ID NO 8)
``` is used to produce a fragment of 930 bp, then after digestion and isolation a BglII-XhoI fragment of about 900 bp. This fragment is called fragment D. Fragment C and fragment D are ligated with the expression plasmid pVR1012, previously digested with BglII and EcoRV, to give the plasmid pJCA162 (8327 bp).

For C Spain Olot, the oligonucleotide pair:

```
JCA313 (37 mer)   5'TTTTGATATCATGGGAGCTGGGCAATCCAGCCCAGCG 3'   (SEQ ID NO 9)
and JCA314 (23 mer)   5'TTCACGACAAACGTGCTGTCCAG 3'                  (SEQ ID NO 10)
``` is used during the first PCR reaction to produce a fragment of 2568 base pairs (bp), then after digestion and isolation a fragment EcoRV-XhoI of about 2540 bp. This fragment is called fragment E.

During the second PCR reaction, the pair of oligonucleotides:

```
JCA315 (21 mer)   5'AGAGCAACCGGAAGCTGAAGG 3'                   (SEQ ID NO 11)
and JCA316 (34 mer)   5'TTTTAGATCTTCAAAGCTTGGTTTTGCGCATTAC 3',     (SEQ ID NO 12)
``` is used to produce a fragment of 947 bp, then after digestion and isolation a fragment BglII-XhoI of about 900 bp. This fragment is called fragment F. Fragment E and fragment F are ligated with the expression plasmid pVR1012, previously digested with BglII and EcoRV, to give the plasmid pJCA163 (8312 bp).

For A24, the oligonucleotide pair:

```
JCA317 (37 mer)   5'TTTTGATATCATGGGGGCCGGGCAATCCAGTCCGGCG 3'   (SEQ ID NO 13)
and JCA318 (31 mer)   5'TTTTCTCGAGGGGGGCCGGCACGTGAAAGAG 3',        (SEQ ID NO 14)
``` is used during the first PCR reaction to produce a fragment of about 2630 base pairs (bp), then after digestion and isolation a fragment EcoRV-XhoI of about 2580 bp. This fragment is called fragment G.

During the second PCR reaction, the pair of oligonucleotides:

```
JCA319 (31 mer)   5'TTTTCTCGAGGGACCGGTGAAGAAGCCTGTC 3'         (SEQ ID NO 15)
and JCA320 (37 mer)   5'TTTTAGATCTTCAGCGGCGGAACAGCGCTTTGTCCTC 3'   (SEQ ID NO 16).
``` is used to produce a fragment of about 950 bp, then after digestion and isolation a fragment BglII-XhoI of about 940 bp. This fragment is called fragment H. Fragment G and fragment H are ligated with the expression plasmid pVR1012, previously digested with BglII and EcoRV, to give the plasmid pJCA164 (about 8400 bp in size).

Example 5

Construction of the Expression Plasmid for A24/A10

The cDNA of the foot-and-mouth virus A24 is synthesised as described in Example 3.

A PCR reaction is carried out with 50 µl of the RNA suspension of foot-and-mouth virus A24 (Example 2) and with the following oligonucleotides:

```
JCA317 (37 mer)   (SEQ ID NO 13)
and
```

-continued
```
JCA321 (24 mer)   (SEQ ID NO 17)
5'TTTGACCTAACGTCGGAGAAGAAG 3'.
```

A fragment of about 2300 bp is produced.

This fragment is then digested with EcoRV then with HindIII to isolate the fragment EcoRV-HindIII of about 1710 [bp], after agarose gel electrophoresis. This fragment is called fragment I.

The fragment of 2300 bp is digested with HindIII then with ApaI to isolate, after agarose gel electrophoresis, the fragment HindIII-ApaI of about 550 bp. This fragment is called fragment J.

The plasmid pJCA161 (Example 3) is digested with ApaI then with EcoRV to isolate the fragment ApaI-EcoRV of about 5960 bp after agarose gel electrophoresis. This fragment is called fragment K.

The fragments I, J and K are ligated together to give the plasmid pJCA165 (8333 bp). This plasmid contains an insert coding for the structural part of the polyprotein A24 and for the enzymatic part of A10, these parts being sufficient to generate capsid proteins capable of self-assembly.

Example 6

Construction of the Recombinant Vaccinia Virus vV100 (A10)

A PCR reaction is carried out using the plasmid pJCA161 (Example 3) as matrix and the following oligonucleotides:

```
JCA322 (37 mer)  5'TTTTGAATTCATGCAGTCCAGCCCAGCAACCGGCTCG 3':        (SEQ ID NO 18)
and JCA323 (44 mer)  5'TTTTGAATTCATAAAAATCAAAGCTTTGTTTTGCGCATCACGTG 3': (SEQ ID NO 19)
``` to amplify a fragment of about 3462 bp.

This pair of oligonucleotides makes it possible to incorporate a restriction site EcoRI at each end of the amplification fragment.

The conditions of the PCR reaction in the presence of this pair of oligonucleotides are a temperature of 95° C. for 2 min, then 35 cycles (95° C. for 1 min, then 62° C. for 1 min, and 72° C. for 2 min), and finally 72° C. for 7 min.

This fragment is digested with EcoRI to isolate the fragment EcoRI-EcoRI of 3448 bp, after agarose gel electrophoresis.

A PCR reaction on the genome of the vaccinia virus (strain WR) is carried out with the oligonucleotide pair:

```
JCA342 (28 mer)
5' TTTTATCGATTCATTGATAGTACCAAAT 3'    SEQ ID NO 40

JCA343 (20 mer)
5' ATTCTACAGTTCTAACATCG 3'.           SEQ ID NO 41
```

The conditions of PCR are the same as before. A 488 bp fragment is produced. This fragment is digested with ClaI and EcoRI, to isolate the fragment of 367 bp, after agarose gel electrophoresis. This last fragment is then inserted in the plasmid pGS20 (Mackett et al., J; Virol., 1984, 49, 857-864), previously digested with ClaI and EcoRI. The plasmid thus obtained is straightened with EcoRI and the fragment EcoRI-EcoRI of 3448 bp is inserted therein, giving the vector pJCA166.

Advantageously, the skilled person can also use the plasmid pvFOHC (Newton et al., in: Vaccines 87, 1987, Chanock et al. eds., Cold Spring Harbor Laboratory, 12-21) containing the P11K promoter of the vaccinia virus and two branches of the TK gene of the vaccinia virus, one upstream of this promoter and the other downstream of an EcoRI site.

Insertion sites in the vaccinia virus other than the TK gene may be used, notably for example the gene HA, M2L.

The plasmid pJCA166 is transfected into COS cells (renal cells from African green monkeys, deposited at the American Type Culture Collection under accession number ATCC CRL-1651) infected with the vaccinia virus (strain WR, ATCC number VR-119).

The COS cells are cultivated in Petri dishes in DMEM culture medium (Dulbecco's Modified Eagles Medium) supplemented with 10% of foetal calf serum, 2 mM of glutamine, 500 UI/µg/ml of penicillin/streptomycin, 12.5 µg/ml of fungizone (all in final concentrations), containing about 100,000 cells per ml, at +37° C. in an atmosphere containing 5% of CO2 for 16 h. When the cells reach 75% confluence, the culture medium is removed. The COS cells are then infected with vaccine virus (strain WR) at a multiplicity of infection (moi) of 3 DICC50/cell, then the dishes are incubated for 1 h. The cultures are then washed with the serum-free DMEM medium. Then 400 µl of a mixture of plasmid/lipofectin/Optimem (8 µl of lipofectin, 192 µl of Optimem and 200 µl of distilled water containing 8 µg of plasmid) are added to each dish, the plasmid being pJCA166. The dishes are incubated at +37° C. in an atmosphere containing 5% of CO2 for 4 to 6 h, stirring every 30 min. Then DMEM medium supplemented with 10% of foetal calf serum is added to each dish and the dishes are incubated at +37° C. in an atmosphere containing 5% of CO2 for 16 h.

The cells can then be harvested, frozen and stored at −20° C.

The selection of the recombinant vaccinia viruses is carried out on 143 TK-human cell cultures (obtainable from the American Type Culture Collection under accession number CRL-8303) in 6 cm dishes containing 5 ml of DMEM culture medium, incubated at +37° C. in an atmosphere containing 5% of CO2 for 16 h.

The transfection suspension obtained previously is added. After 1 hour's incubation at +37° C., 25 µg of 5-bromodesoxyuridine (BUdR) per ml is added in order to select the recombinants vaccinia viruses TK-. Incubation is extended for 48 h to allow the development of the recombinant cells. 3 successive cycles of selection/purification of recombinant vaccinia virus are carried out.

24 well plates are seeded with 143 TK-cells with DMEM medium containing 25 µg of BUdR per ml. After 2 h of incubation at +37° C. about 10 spots each taken up in 2 µl of PBS buffer are transferred into in 10 wells. The spots are then incubated for 48-72 h.

After incubation, a PCR reaction is carried out on the culture supernatant of each well using the <<Gene Releaser>> method (Cambio) with oligonucleotides JCA305 and JCA308.

For the wells found to be positive the recombinant virus undergoes a fresh cycle of purification. The recombinant virus known as vV100 is amplified and stored at −70° C. or −20° C.

Example 7

Construction of the Recombinant Viruses of the Vaccine for Types O, C and A

The constructions of the recombinant vaccinia viruses are obtained for types O, C and A of the foot-and-mouth viruses as described in Example 6.

For type O:

The PCR reaction is carried out using the plasmid pJCA162 (Example 4) as matrix and the following oligonucleotides:

```
JCA324 (37 mer)  5' TTTTGAATTCATGGGGGCTGGACAATCCAGTCCAGCG 3':    (SEQ ID NO 20)
and JCA325 (41 mer)  5' TTTTGAATTCATAAAAATCAAAGCTTGGTTTTGCGCATCAC 3':  (SEQ ID NO 21)
``` to amplify a fragment of about 3470 bp.

After digestion and isolation, the fragment EcoRI-EcoRI of 3448 bp is inserted in the plasmid pvFOHC, previously digested with EcoRI, to give the donor plasmid pJCA167.

Recombination is effected according to the technique described in Example 6. Positive areas are selected by PCR reaction with oligonucleotides JCA309 and JCA312. One area is amplified and the stock of recombinant virus obtained is designated vV101.

For type C:

The PCR reaction is carried out using the plasmid pJCA163 (Example 4) as matrix and the following oligonucleotides:

```
JCA326 (37 mer)  5' TTTTGAATTCATGGGAGCTGGGCAATCCAGCCCAGCG 3'      (SEQ ID NO 22)
and JCA327 (41 mer)  5' TTTTGAATTCATAAAAATCAAAGCTTGGTTTTGCGCATTAC 3': (SEQ ID NO 23)
``` to amplify a fragment of about 3460 bp.

After digestion and isolation, the fragment EcoRI-EcoRI of 3439 bp is inserted in the plasmid pvFOHC, previously digested with EcoRI, to give the donor plasmid pJCA168.

Recombination is carried out according to the technique described in Example 6. Positive plaques are selected by PCR reaction with the oligonucleotides JCA313 and JCA316. A plaque is amplified and the stock of recombinant virus obtained is designated vV102.

For type A:

The PCR reaction is carried out using the plasmid pJCA164 (Example 4) as matrix and the following oligonucleotides:

```
JCA328 (37 mer)  5' TTTTGAATTCATGGGGGCCGGGCAATCCAGTCCGGCG 3':   (SEQ ID NO 24)
and JCA329 (44 mer)  5' TTTTGAATTCATAAAAATCAGCGGCGGAACAGCGCTTTGTCCTC 3':  (SEQ ID NO 25)
``` to amplify a fragment of about 3550 bp.

After digestion and isolation, the fragment EcoRI-EcoRI of about 3530 bp is inserted in the plasmid pvFOHC, previously digested with EcoRI, to give the donor plasmid pJCA169.

The recombination is carried out using the technique described in Example 6. Positive plaques are selected by PCR reaction with the oligonucleotides JCA317 and JCA320. A plaque is amplified and the stock of recombinant virus obtained is designated vV103.

Type A variant:

The PCR reaction is carried out using the plasmid pJCA165 (Example 5) as matrix and the following oligonucleotides:

JCA328 (SEQ ID NO 24) (37 mer)

and JCA325 (SEQ ID NO 21) (37 mer)

to amplify a fragment of about 3480 bp.

After digestion and isolation, the fragment EcoRI-EcoRI of about 3463 bp is inserted in the plasmid pvFOHC, previously digested with EcoRI, to give the donor plasmid pJCA170.

The recombination is carried out using the technique described in Example 6. Positive plaques are selected by PCR reaction with the oligonucleotides JCA317 and JCA312. A plaque is amplified and the stock of recombinant virus obtained is designated vV104.

Example 8

Construction of Recombinant Viruses of the Vaccine for the Expression In Vitro (A10)

The plasmid pJCA161 (Example 3) is digested with the restriction enzymes EcoRV and BglII. After agarose gel electrophoresis, a fragment EcoRV-BglII about 3450 bp in size is isolated. This fragment is made "blunt-ended" by treating with Klenow polymerase, then ligated into the plasmid pBG200 (Abrams et al., 1995, J. Gen. Virol., 76, 3089-3098), which has previously been digested with BamHI and made blunt-ended by treating with Klenow polymerase, to give the donor plasmid pJCA171.

The plasmid pBG200 contains the T7 bacteriophage promoter, the T7 transcription terminator and two branches of the TK gene of the vaccinia virus, one upstream of this promoter and the other downstream of the terminator (the skilled man may refer to Fuerst et al., Molecular and Cellular Biology, 1987, 7, 2538-2544 for the construction of pBG200). The BamHI insertion site on the plasmid pBG200 is located between the promoter and the terminator of T7.

The recombination is carried out using the technique described in Example 6. Positive plaques are selected by PCR reaction with the oligonucleotides JCA305 and JCA308. A plaque is amplified and the stock of recombinant virus obtained is designated vV105.

The stock of recombinant virus is preserved at −20° C. or −70° C.

Example 9

Construction of the Recombinant Vaccinia Viruses for In Vitro Expression of Types O, C and A The constructions of the recombinant vaccinia viruses for in vitro expression are obtained for types O, C and A of the foot-and-mouth viruses as described in Example 8.

For type O:

The plasmid pJCA162 (Example 4) is digested with the restriction enzymes EcoRV and BglII. After isolation, an EcoRV-BglII fragment about 3450 bp in size is made blunt-ended by treating with Klenow polymerase, then ligated into the plasmid pBG200 previously digested with BamHI and made blunt-ended by treating with Klenow polymerase, to give the donor plasmid pJCA172.

A plaque selected by PCR reaction with the oligonucleotides JCA309 and JCA312 is amplified and the stock of recombinant virus obtained is designated vV106.

For type C:

The plasmid pJCA163 (Example 4) is digested with the restriction enzymes EcoRV and BglII. After isolation, a fragment EcoRV-BglII about 3440 bp in size is made blunt-ended by treating with Klenow polymerase, then ligated into the plasmid pBG200 previously digested with BamHI and made blunt-ended by treating with Klenow polymerase, to give the donor plasmid pJCA173.

A plaque selected by PCR reaction with the oligonucleotides JCA313 and JCA316 is amplified and the stock of recombinant virus obtained is designated vV107.

For type A:

The plasmid pJCA164 (Example 4) is digested with the restriction enzymes EcoRV and BglII. After isolation, a fragment EcoRV-BglII about 3520 bp in size is made blunt-ended by treating with Klenow polymerase, then ligated into the plasmid pBG200 previously digested with BamHI and made blunt-ended by treating with Klenow polymerase, to give the donor plasmid pJCA174.

A plaque selected by PCR reaction with the oligonucleotides JCA317 and JCA320 is amplified and the stock of recombinant virus obtained is designated vV108.

Type A variant:

The plasmid pJCA165 (Example 5) is digested with the restriction enzymes EcoRV and BglII. After isolation, a fragment EcoRV-BglII about 3450 bp in size is made blunt-ended by treating with Klenow polymerase, then ligated into the plasmid pBG200 previously digested with BamHI and made blunt-ended by treating with Klenow polymerase, to give the donor plasmid pJCA175.

A plaque selected by PCR reaction with the oligonucleotides JCA317 and JCA312 is amplified and the stock of recombinant virus obtained is designated vV109.

Example 10

Production and Purification of Empty Viral Capsids

Rabbit kidney cells RK13 (obtainable from the American Type Culture Collection under accession number CCL-37) are cultivated at 37° C. in twenty 175 cm2 Falcons with 20 ml of DMEM medium supplemented with 10% of foetal calf serum, 2 mM of glutamine, 500 UI/µg/ml of penicillin/streptomycin, 12.5 µg/ml of fungizone, each Falcon contains about 2×107 cells at confluence.

The recombinant vaccinia viruses vTF7-3 and vV108 (Example 9) are then each added at a multiplicity of infection (moi) of 10 DICC50/cell in each Falcon. The vral culture is kept at 37° C. for about 24 hours until a 100% cytopathogenic effect is obtained.

The recombinant vaccinia virus vTF7-3 (obtainable from the ATCC under number VR-2153) contains the RNA polymerase of the bacteriophage T7 under the control of the p7.5K promoter of the vaccinia virus (Fuerst et al., 1986, Proc. Natl. Acad. Sci. USA, 83, 8122-8126).

The production of the RNA polymerase T7 induces the expression of the insert under the control of the T7 promoter. The P1 precursor and the 3C protease of the foot-and-mouth viruses are thus produced and the empty capsids assemble themselves.

The viral suspension is harvested then clarified by centrifugation (4,000 revolutions per minute (rpm), for 30 min, at 4° C.).

The residue is resuspended in 30 ml of phosphate buffer (40 mM of sodium phosphate, 100 mM of sodium chloride, pH 7.6) at 0° C., containing 0.5% of Nonidet P40 (Roche, Cat. No. 1 754 599). Cell lysing is carried out at 0° C. on ice for 20 min.

The cell debris is harvested after centrifugation at 10,000 rpm, for 20 min, at 4° C. The supernatant is preserved at 0° C., on ice. The cell debris is resuspended in 6 ml of phosphate buffer. Extraction is carried out with chloroform (in equal volumes). The aqueous phase obtained from this extraction, mixed with the supernatant obtained previously, is deposited on a 15% saccharose cushion (2 ml) and centrifuged with a Beckman SW28 rotor (28,000 rpm, 5 hours, 4° C.). The residue is taken up in 1 ml of phosphate buffer and stored at 4° C.

The residue obtained is resuspended, then treated with 20 µl of RNase (10 mg/ml) on ice for 10 min. 10 µl of 10% Nonidet P40 are then added and the whole thing is left on ice for 10 min. The suspension is then extracted with an equal volume of chloroform. The aqueous phase (1 ml) is recovered and deposited on a 15-45% saccharose gradient (about 12 ml) and centrifuged with a Beckman SW40 rotor (40,000 rpm, 5 hours, 12° C. or 18,000 rpm, 16 hours, 12° C.).

The gradient is then fractionated into 14 fractions of 0.8 ml. The absorption is measured at a wavelength of 220 nm. The fractions corresponding to the absorption peak are harvested. These fractions contain the empty viral capsids A24. The specificity of the proteins harvested is verified by Western Blot.

The empty viral capsids of sub-types O1K, A10, C Spain Olot and A24/A10 are obtained by exactly the same method as described in this Example, by replacing the recombinant vaccinia viruses vV108 with vV106 (Example 9), vV105 (Example 8), vV107 (Example 9) and vV109 (Example 9), respectively.

The protein fractions thus obtained are preserved at 4° C. before being used in vaccines.

Example 11

Production of Sub-unit Vaccines 13.2 ml of the fractions of the saccharose gradient containing a total of 165 µg of empty foot-and-mouth virus capsids, obtained in Example 10, are formulated with 14.01 ml of DMEM containing 27.5 ml of 1.5% aluminium hydroxide (Al(OH)3) and 0.29 ml of saponine.

The 55 ml thus obtained are then divided between two flasks, 30 ml in the first and 25 ml in the second. A dose of 5 ml contains 15 µg of empty viral capsids with 360 haemolytic units of saponine.

The quantity of empty particles is determined par spectrophotometry by measuring the adsorption at 220 nm using a bovine serum albumin solution (BSA) as standard Example 12

Production of Recombinant Vaccines

To prepare vaccines, the recombinant vaccinia viruses vV100 to vV105 (Examples 6 and 7) may be combined with solutions of carbomer. The preferred carbomer is CarbopolTM 974P made by BF Goodrich, Ohio, USA (molecular weight of about 3,000,000).

A 1.5% stock solution of CarbopolTM 974P is initially prepared in distilled water containing 1 g/l of sodium chloride. This stock solution is then used to prepare a solution of 4 mg/ml of CarbopolTM 974P in physiological saline. The stock solution is mixed with a suitable volume of physiological saline, either in a single step or in a number of successive steps, the pH is adjusted in each step with a 1N (or more concentrated) sodium hydroxide solution to obtain a final pH of 7.3-7.4.

The CarbopolTM 974P solution ready for use thus obtained can be used to take up lyophilised recombinant viruses or to dilute concentrated stock solutions of recombinant viruses. For example, to obtain a viral suspension containing 108 pfu per dose of 1 ml, a viral stock solution is diluted to obtain a titre of 108,3 pfu/ml, then it is diluted in equal parts with said ready-to-use 4 mg/ml solution of CarbopolTM 974P.

Example 13

Production of DNA Vaccines

A DNA solution containing one or more plasmids pJCA161 to pJCA165 (Examples 3 and 4) is concentrated by ethanol precipitation as described in Sambrook et al (1989). The DNA residue is taken up in a 0.9% NaCI solution so as to obtain a concentration of 1 mg/ml. A 0.75 mM solution of DMRIE-DOPE is prepared by taking up a lyophilisate of DMRIE-DOPE in a suitable volume of sterile $H_2O$ (DMRIE or N-(2-hydroxyethyl)-N,N-dimethyl-2,3-bis(tetradecyloxy)-1-propanammonium (WO-A-9634109); DOPE or dioleoyl-phosphatidyl-ethanolamine (Behr J. P., 1994, Bioconjugate Chemistry, 5, 382-389)).

The plasmid DNA-lipid complexes are formed by diluting equal parts of the 0.75 mM solution of DMRIE-DOPE with the 1 mg/ml DNA solution in 0.9% NaCI. The DNA solution is added progressively using a crimped 26G needle along the wall of the flask containing the cationic lipid solution, to prevent foaming. The flask is agitated gently as soon as the two solutions are mixed. Finally, a composition is obtained which contains 0.375 mM of DMRIE-DOPE and 500 pg/ml of plasmid.

All the solutions used should be at ambient temperature for all the procedures described hereinbefore. The DNA/DMRIE-DOPE complexing is left to take place at ambient temperature for 30 minutes before the animals are immunised.

Example 14

Testing on Cattle

The vaccine against foot-and-mouth virus A24, obtained in Example 11 from the empty viral capsids expressed by vV109, is administered to a group of 6 cattle.

The injection is carried out by subcutaneous route, each side of the neck, facing the shoulders. The first 5 animals are given a dose of 5 ml (2×2.5 ml), the 6th animal being given 4 ml (2×2.0 ml). This 6th animal is tattooed on the ear with the symbol <<UC10>>.

Each animal is given a second injection by subcutaneous route on each side of the neck 31 days after the first vaccination (4 ml for the first 5 animals (2×2.0 ml) and 0.5 ml (2×0.25 ml) for the 6th animal).

Blood samples are taken from the animals vaccinated on day 0 (date of first vaccination), d6, d13, d20, d31, d38, d42, d52 and immediately before slaughtering.

All the vaccinated animals and 2 non-vaccinated control animals are challenged by intradermolingual route (10×0.10 ml per tongue) with A24 foot-and-mouth viruses in a titre of $10^{4,4}$ infectious doses/ml (titre on bovine thyroid cells). The challenge takes place 42 days after the first vaccination.

Each animal is checked daily for temperature (table 2) and for signs of foot-and-mouth disease on the tongue, in the mouth and on the feet (table 1). The levels of neutralising anti-foot-and-mouth virus A24 antibodies are monitored (FIG. 1).

TABLE 1

Monitoring of clinical signs of foot-and-mouth disease in the cattle after virulent challenge

| Animal/day after challenge | 0 | 1 | 2 | 3 | 4 | 5 | 6 | 7 | 8 | 9 | 10 |
|---|---|---|---|---|---|---|---|---|---|---|---|
| Vaccinated UC6 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |
| Vaccinated UC7 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |
| Vaccinated UC8 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |
| Vaccinated UC9 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |
| Vaccinated UC10 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |

TABLE 1-continued

Monitoring of clinical signs of foot-and-mouth disease in the cattle after virulent challenge

| Animal/day after challenge | 0 | 1 | 2 | 3 | 4 | 5 | 6 | 7 | 8 | 9 | 10 |
|---|---|---|---|---|---|---|---|---|---|---|---|
| Vaccinated UC11 | T0 | T1 | T1 | T1 | T1 | T1 | ND | T1 | T0 | ND | T0 |
|  | 4F0 | 4F0 | 4F0 | 4F0 | 4F0 | 4F0 |  | 4F0 | 4F0 |  | 4F0 |
| Control UC79 | T0 | T1 | T2 | T2 | T2 | T2 | T2 | T2 | T2 | T2 | T2 |
|  | 4F0 | 4F0 | 4F0 | 4F0 | 4F0 | 4F+ | 4F+ | 4F+ | 4F+ | 4F+ | 4F+ |
| Control UC80 | T0 | T1 | T2 | T2 | T2 | T2 | T2 | T2 | T2 | T2 | T2 |
|  | 4F0 | 4F0 | 4F0 | 4F0 | 4F0 | 4F+ | 4F+ | 4F+ | 4F+ | 4F+ | 4F+ |

Explanation of codes:
T0: healthy tongue, no sign of viral replication, no trace at injection sites
T1: healthy tongue, no sign of viral replication, only trauma at injection sites
T2: presence of primary lesions on the tongue
T3: presence of primary and secondary lesions on the tongue or in other parts of the mouth
4F0: no sign of foot-and-mouth disease on all four feet
4F+: presence of vesicles on all fur feet.
ND: no clinical trial carried out These results show that the vaccinated animals are all protected against infection by the foot-and-mouth virus A24, even locally at the injection sites. The animal UC10 which was given a weaker booster injection than the others is also protected. Conversely, the control animals prone to infection by the virus visibly develop the disease in the mouth on the second day after the challenge and on their feet the fifth day after the challenge.

TABLE 2

Monitoring the temperatures (in ° C.) of the cattle after virulent challenge

| Animal/day after challenge | 0 | 1 | 2 | 3 | 4 | 5 | 6 | 7 | 8 | 9 | 10 |
|---|---|---|---|---|---|---|---|---|---|---|---|
| Vaccinated UC6 | 38.6 | 38.6 | 38.2 | 37.9 | 38.2 | 38.6 | 38.5 | 38.7 | 38.5 | 39.1 | 39.1 |
| Vaccinated UC7 | 38.7 | 38.5 | 38.4 | 38.2 | 38.3 | 38.2 | 38.3 | 38.5 | 38.6 | 38.4 | 38.0 |
| Vaccinated UC8 | 38.3 | 39.0 | 38.3 | 38.5 | 38.6 | 38.6 | 38.5 | 38.3 | 38.2 | 38.0 | 38.6 |
| Vaccinated UC9 | 38.8 | 38.7 | 39.0 | 38.6 | 38.4 | 38.5 | 38.3 | 38.4 | 38.6 | 38.8 | 39.0 |
| Vaccinated UC10 | 39.3 | 38.8 | 38.9 | 38.6 | 38.6 | 38.7 | 38.8 | 39.0 | 38.7 | 39.2 | 39.1 |
| Vaccinated UC11 | 38.6 | 38.8 | 38.4 | 38.3 | 38.3 | 38.0 | 38.2 | 38.0 | 38.3 | 38.7 | 38.8 |
| Control UC79 | 39.0 | 40.7 | 41.0 | 39.5 | 39.6 | 38.8 | 38.4 | 38.6 | 38.4 | 38.6 | 38.8 |
| Control UC80 | 39.1 | 39.8 | 40.6 | 39.9 | 39.4 | 38.9 | 38.6 | 38.5 | 38.9 | 38.8 | 38.6 |

These results show that the vaccinated cattle do not exhibit any hyperthermia, even the animal UC10 which was given a weaker booster injection than the others. Conversely, the control cattle do have hyperthermia, which reaches its peak two days after the challenge, followed by a return to normal body temperatures.

FIG. 1 shows that the vaccinated cattle develop a strong response of neutralising anti-foot-and-mouth virus A24 antibodies with a first peak about 13 days after the first vaccination. After the booster injection, a strong response of neutralising antibodies is observed. This is also observed in the animal UC10 which was given a weaker booster injection than the others. After challenge, the antibody level does not increase, indicating that the FDMV A24 virus is not replicating sufficiently to stimulate the antibody response.

In conclusion, the vaccine against foot-and-mouth disease A24 produced from empty viral capsids obtained from recombinant vaccinia virus expression vectors induces a primary and secondary immune response in cattle. After challenge, these cattle are fully protected against foot-and-mouth disease and against viral replication.

Example 15

Mutagenesis on the A10 Construction

Mutagenesis directed to the A10 construction is carried out using oligonucleotides and PCR reactions with the aim of replacing the codon coding for the histidine 179 (position in the polyprotein coded by the plasmid pJCA161, Example 3; the methionine initiator being numbered 1) by a codon coding for a cysteine.

A PCR reaction is carried out using the plasmid pJCA161 as matrix and the following oligonucleotides:

```
JCA309 (37 mer)                                     (SEQ ID NO 5)
and
JCA330 (27 mer)
5' TGAGTCCACCAGGCACCCGAAGACACC 3':  (SEQ ID NO 26)
``` to amplify a 559 bp fragment. This fragment is called fragment L.

The conditions of the first cycle of the PCR reaction are 95° C. for 2 min, then 62° C. for 2 min and 72° C. for 3 min.

The conditions of the following 35 cycles of the PCR reaction are the same as described in Example 6.

A second PCR reaction is carried out using the plasmid pJCA161 as matrix and the following oligonucleotides:

```
JCA331 (27 mer)  5' GGTGTCTTCGGGTGCCTGGTGGACTCA 3':         (SEQ ID NO 27)
and JCA332 (36 mer)  5' AAAGTCTTTGCCGGCGCTAGCCGACACTAACAAGGT 3':  (SEQ ID NO 28)
``` to amplify a fragment of 1020 bp. This fragment is called fragment M.

The conditions of the PCR reaction are the same as described in Example 6.

A third PCR reaction is carried out using the fragments L and M as matrix, and the oligonucleotides JCA309 (SEQ ID NO 5) and JCA332 (SEQ ID NO 28) to amplify a fragment of 1552 bp. The conditions of the PCR reaction are the same as described in Example 6.

This fragment is then digested using EcoRV and NheI, to isolate the 1527 bp EcoRV-NheI fragment, after agarose gel electrophoresis. This fragment is called fragment N.

The plasmid pJCA161 is digested with NheI then with EcoRV to isolate the NheI-EcoRV fragment of about 6800 bp, after agarose gel electrophoresis. This fragment and fragment N are ligated together to give the plasmid pJCA176 (8327 bp). This plasmid contains an insert coding for the part of the polyprotein A10 sufficient to generate heat-stable mutated capsid proteins capables of self-assembly.

The plasmid pJCA176 is used to construct a recombinant vaccinia virus according to Example 8, the fragment EcoRV-BglII being obtained in this case from the plasmid pJCA176 and not from the plasmid pJCA161 The recombinant virus thus obtained is called vV110.

Example 16

Mutagenesis on the O1K Construction

Mutagenesis directed to the O1K construction is carried out using oligonucleotides and PCR reactions as described in Example 15, with the aim of replacing the codon coding for the serine 179 (position in the polyprotein coded by the plasmid pJCA162, Example 4; the methionine initiator being numbered 1) by a codon coding for a cysteine.

A PCR reaction is carried out using the plasmid pJCA162 as matrix and the following oligonucleotides:

```
JCA305 (37 mer)                                     (SEQ ID NO 1)
and

JCA333 (27 mer)
5' CGAGTCAGTCAGGCAGCCGTAGACACC 3':  (SEQ ID NO 29)
``` to amplify a fragment of 559 bp. This fragment is called fragment O.

A second PCR reaction is carried out using the plasmid pJCA162 as matrix and the following oligonucleotides

```
JCA334 (27 mer)  5' GGTGTCTACGGCTGCCTGACTGACTCG 3'            (SEQ ID NO 30)
and JCA335 (36 mer)  5' AGACGTCCGTGTGTTGGCGCCTCTGGATCTGTGTTT 3':  (SEQ ID NO 31)
``` to amplify a fragment of 1147 bp. This fragment is called fragment P.

A third PCR reaction is carried out using the fragments O and P as matrix, and the oligonucleotides JCA305 (SEQ ID NO 1) and JCA335 (SEQ ID NO 31) to amplify a fragment of 1679 bp.

This fragment is then digested using EcoRV and of NarI, to isolate the 1654 bp EcoRV-NarI fragment, after agarose gel electrophoresis. This fragment is called fragment Q.

The plasmid pJCA162 is digested with NarI then with EcoRV to isolate the fragment NarI-EcoRV of about 6670 bp, after agarose gel electrophoresis. This fragment and fragment Q are ligated together to give the plasmid pJCA177 (8327 bp). This plasmid contains an insert coding for the part of the polyprotein O1K sufficient to generate heat-stable mutated capsid proteins capable of self-assembly.

The plasmid pJCA177 is used to construct a recombinant vaccinia virus according to Example 9, the fragment EcoRV-BglII being obtained in this case from the plasmid pJCA177 and not from the plasmid pJCA162. The recombinant virus thus obtained is called vV111.

Example 17

Mutagenesis on the C Spain Olot Construction

Mutagenesis directed to the C Spain Olot construction is carried out using oligonucleotides and PCR reactions as described in Example 15, with the aim of replacing the codon coding for the glycine 179 (position in the polyprotein coded by the plasmid pJCA163, Example 4; the methionine initiator being numbered 1) by a codon coding for a cysteine.

A PCR reaction is carried out using the plasmid pJCA163 as matrix and the following oligonucleotides:

```
JCA313 (37 mer)                                      (SEQ ID NO 9)
and

JCA336 (27 mer)
5' TGACTTGACGAGGCACCCGTAAACACC 3':  (SEQ ID NO 32)
``` to amplify a fragment of 559 bp. This fragment is called fragment R.

A second PCR reaction is carried out using the plasmid pJCA163 as matrix and the following oligonucleotides:

```
JCA337 (27 mer)  5' GGTGTTTACGGGTGCCTCGTCAAGTCA 3':           (SEQ ID NO 33)
and JCA338 (36 mer)  5' GTAGTACTGGGCCAAGCCGGCCAAGTAGGTGTTTGA 3':  (SEQ ID NO 34)
``` to amplify a fragment of 681 bp. This fragment is called fragment S.

A third PCR reaction is carried out using the fragments R and S as matrix, and the oligonucleotides JCA313 (SEQ ID

```
JCA340 (27 mer)  5' GGTGTCTTTGGATGCTTGGTGGACTCG 3'            (SEQ ID NO 36)
and JCA341 (36 mer)  5' CCCAGGGTAGTTAGTCCTAGGCGGGTTGTACACCTT 3':  (SEQ ID NO 37)
```

NO 9) and JCA338 (SEQ ID NO 34) to amplify a fragment of 1213 bp.

This fragment is then digested with EcoRV and NaeI, to isolate the fragment EcoRV-NaeI of about 1190 bp, after agarose gel electrophoresis. This fragment is called fragment T.

The plasmid pJCA163 is digested with NaeI then with EcoRV to isolate the fragment NaeI-EcoRV of about 7120 bp, after agarose gel electrophoresis. This fragment and the fragment T are ligated together to give the plasmid pJCA178 (8312 bp). The plasmid pJCA178 contains an insert coding for the part of the polyprotein C Spain Olot sufficient to generate heat-stable mutated capsid proteins capable of self-assembly.

The plasmid pJCA178 is used to construct a recombinant vaccinia virus according to Example 9, the fragment EcoRV-BglII being obtained in this case from the plasmid pJCA178 and not from the plasmid pJCA163. The recombinant virus thus obtained is called vV112.

Example 18

Mutagenesis on the A24 Construction

Mutagenesis directed to the A24 construction is carried out using oligonucleotides and PCR reactions as described in Example 15, with the aim of replacing the codon coding for the histidine 179 (position in the polyprotein coded by the plasmid pJCA164, Example 4; the methionine initiator being numbered 1) by a codon coding for a cysteine.

A PCR reaction is carried out using the plasmid pJCA164 as matrix and the following oligonucleotides:

```
JCA317 (37 mer)                                      (SEQ ID NO 13)
and

JCA339 (27 mer)
5' CGAGTCCACCAAGCATCCAAAGACACC 3':  (SEQ ID NO 35)
``` to amplify a fragment of 559 bp. This fragment is called fragment U.

A second PCR reaction is carried out using the plasmid pJCA164 as matrix and the following oligonucleotides:

to amplify a fragment of 507 bp. This fragment is called fragment V.

A third PCR reaction is carried out using the fragments U and V as matrix, and the oligonucleotides JCA317 (SEQ ID NO 13) and JCA341 (SEQ ID NO 37) to amplify a fragment of 1039 bp.

This fragment is then digested with EcoRV and BlnI, to isolate the EcoRV-BlnI fragment of about 1014 bp, after agarose gel electrophoresis. This fragment is called fragment W.

The plasmid pJCA164 is digested with BlnI then with EcoRV to isolate the BlnI-EcoRV fragment of about 7360 bp, after agarose gel electrophoresis. This fragment and fragment W are ligated together to give the plasmid pJCA179 (about 8400 bp in size). This plasmid contains an insert coding for the part of the polyprotein A24 sufficient to generate heat-stable mutated capsid proteins capable of self-assembly.

The plasmid pJCA179 is used to construct a recombinant vaccinia virus according to the Example 9, the fragment EcoRV-BglII being obtained in this case from the plasmid pJCA179 and not from the plasmid pJCA164 The recombinant virus thus obtained is called vV113.

Example 19

Production and Purification of Heat-Stable Empty Viral Capsids

The modified empty viral capsids sub-types A10, O1K, C Spain Olot and A24 are obtained by exactly the same method as described in Example 10, by replacing the recombinant vaccinia viruses vV108 with vV110 (Example 15), vV111 (Example 16), vV112 (Example 17) and vV113 (Example 18), respectively.

Example 20

Monitoring Heat Stability 10 tubes containing modified empty viral capsids (Example 19) of foot-and-mouth virus A10 are prepared and quantified. Each tube contains 0.8 µg of capsids in 0.5 ml of phosphate buffer, pH 7.6.

These 10 tubes are placed in a water bath at 50° C. for 1 hour. Then they are cooled. Each sample of capsid is placed on a saccharose gradient (15-35%) and centrifuged for 2.5 hours at 12° C. (40,000 rpm with a Beckman SW40 rotor). Each gradient obtained is the fractionated into 12 fractions of 1 ml. 0.5 ml of each fraction is precipitated in the presence of 1 ml of absolute ethanol at −20° C. for 16 hours.

The residue is collected, dried, resuspended in a charging buffer (Maniatis et al., 1982, in: <<Molecular cloning: a laboratory manual>>, Cold Spring Harbor Laboratory, Cold Spring Harbor, N.Y., USA) and deposited on an SDS-PAGE 10% acrylamide electrophoresis gel. The protein bands after transfer are shown up by an anti-140S A10 polyclonal guinea-pig antibody reacting essentially with the protein VP1.

Figure 2:
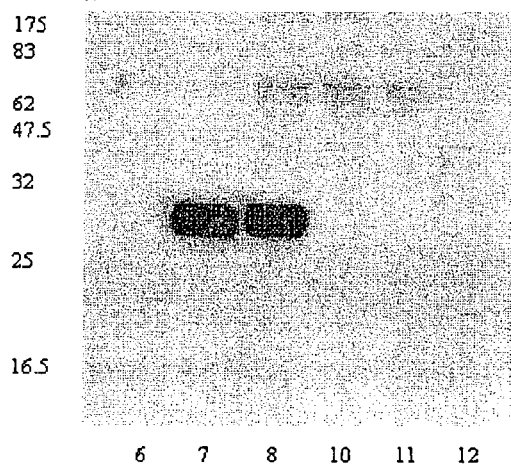
FIG. 2: photography of gels obtained
Figure 2:
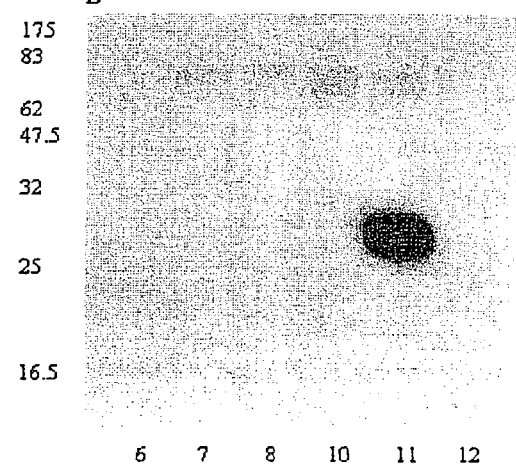

The empty capsids migrate in the gradient at fractions 7 and 8 while the degraded empty capsids stay close to the top of the gradient level with fraction 11. The Western (FIG. 2) shows that the empty capsids corresponding to the mutant are always assembled after 1 h at 50° C. (gel A) whereas the non-mutated empty capsids are degraded, having failed to withstand the heat treatment (gel B) as might be expected.

Example 21

Production of Sub-unit Vaccines Containing Heat-stable Empty Capsids of Foot-and-Mouth Virus The vaccines containing modified empty viral capsids of sub-types O1K, A10, C Spain Olot and A24 of foot-and-mouth virus are obtained by proceeding in a similar manner to that described in Example 11, by replacing the non-modified empty viral capsids with the modified empty viral capsids (Example 19).

It should be realised that the invention as defined by the accompanying claims is not restricted to the particular embodiments described in the foregoing description but covers all the variants within both the scope and spirit of the present invention. ,

---

The invention claimed is:

1. A vaccine or immunogenic composition against foot-and-mouth disease comprising an effective amount of an antigen or an expression vector comprising cDNA encoding said antigen and a veterinarily acceptable vehicle excipient: wherein the antigen comprises empty capsids of foot and mouth disease virus, obtained by expression, in eukaryotic cells, of cDNA encoding a modified P1 region and 3C protease of foot-and-mouth virus, wherein the modified P1 contains a cysteine substitution at the position corresponding to amino acid 179 of SEQ ID NO: 38, which forms a non naturally occurring sulpher-sulpher bond that heat stabilizes the empty capsid.

2. The vaccine or immunogenic composition according to claim 1, wherein the cDNA coding for P1 also codes for all or part of 2A.

3. The vaccine or immunogenic composition according to claim 1, wherein the cDNA coding for 3C also codes for all or part of the proteins 3B.

4. The vaccine or immunogenic composition according to claim 1, wherein the empty capsids are present in the vaccine as sub-units, in an effective amount.

5. The vaccine or immunogenic composition according to claim 4, wherein the empty capsids in the form of sub-units are obtained by expression of the cDNA in eukaryotic cells, by an expression vector in vitro, under the control of an inducible promoter or a late promoter of viral origin.

6. The vaccine or immunogenic composition according to claim 5, wherein the promoter is selected from among T7 bacteriophage promoter, heat-shock promoter or a late promoter of viral origin.

7. The vaccine or immunogenic composition according to claim 6, wherein the promoter is the T7 bacteriophage promoter and the empty capsids in the form of sub-units are obtained by expression of the cDNA in the presence of the expression of T7 polymerase.

8. The vaccine or immunogenic composition according to claim 5, wherein the expression vectors are selected from the group consisting of viral vectors, and plasmid vectors, or wherein the cDNA is integrated in the eukaryotic cells.

9. The vaccine or immunogenic composition according to claim 8, wherein the vector is a pox virus and the late promoter of viral origin is selected from among P11K of the vaccinia virus, P28K of the vaccinia virus and P160K ATI of the cowpox virus.

10. The vaccine or immunogenic composition according to claim 8, wherein the viral vector is a vaccinia virus.

11. The vaccine or immunogenic composition according to claim 9, wherein the poxvirus vector is a vaccinia viral vector.

12. The vaccine or immunogenic composition according to claim 10 wherein the eukaryotic cells are from a cell line, selected from the group consisting of BHK-21, CHO, COS, RK13, Vero, MDBK and PK15 cells.

13. The vaccine or immunogenic composition according to claim 1, wherein it is formulated with a medium for preserving the empty capsids.

14. The vaccine or immunogenic composition according to claim 1, further containing an adjuvant.

15. The vaccine or immunogenic composition according to claim 14, wherein the adjuvant is selected from the group consisting of aluminum hydroxide, saponine, avridine, DDA, a polymer of acrylic or methacrylic acid, a polymer of maleic anhydride and an alkenyl derivative, GM-CSF, a water-in-oil emulsion, oil-in-water emulsion and water-in-oil-in-water emulsion.

16. The vaccine or immunogenic composition according to claim 1, wherein the vaccine contains an expression vector containing cDNA to produce the capsids in vivo.

17. The vaccine or immunogenic composition according to claim 16, wherein the vector is a viral vector or a plasmid vector.

18. The vaccine or immunogenic composition according to claim 17, wherein the vector is a viral vector.

19. The vaccine or immunogenic composition according to claim 16, wherein the cDNA is expressed by a viral vector under the control of a late promoter of viral origin.

20. The vaccine or immunogenic composition according to claim 19, wherein the vector is a poxvirus and the late promoter of viral origin is selected from among P11K of the vaccinia virus, P28K of the vaccinia and P160K ATI of the cowpox virus.

21. The vaccine or immunogenic composition according to claim 19, wherein the cDNA is expressed by a plasmid vector, under the control of a strong early promoter of viral origin or of cellular origin.

22. The vaccine or immunogenic composition according to claim 21, wherein the cDNA is expressed by a plasmid vector, under the control of a promoter selected from the group consisting of the early promoter of the SV40 virus, the LTR promoter of the Rous sarcoma virus, and a promoter of a cytoskeleton gene.

23. The vaccine or immunogenic composition according to claim 18, wherein the viral vector is a poxvirus selected from the group consisting of vaccinia, fowlpox, canarypox, racoonpox, swinepox, and capripox.

24. The vaccine or immunogenic composition according to claim 23, wherein the poxvirus is fowlpox.

25. The vaccine or immunogenic composition according to claim 23, wherein the poxvirus is canarypox.

26. The vaccine or immunogenic composition according to claim 23, wherein the poxvirus is racoonpox.

27. The vaccine or immunogenic composition according to claim 23, wherein the poxvirus is swinepox.

28. The vaccine or immunogenic composition according to claim 23, wherein the poxvirus is capripox.

29. The vaccine or immunogenic composition according to claim 18, wherein the viral vector is selected from the group consisting of adenoviruses and herpesviruses.

30. The vaccine or immunogenic composition according to claim 21, wherein expression of the sequence is under the control of a CMV-IE promoter.

31. The vaccine or immunogenic composition according to claim 22, wherein the cytoskeleton gene is the desmin promoter or the actin promoter.

32. The vaccine or immunogenic composition according to claim 1, wherein the vaccine is formulated with a 9 parts per 1000 NaCl saline solution or a phosphate buffer.

33. The vaccine or immunogenic composition according to claim 16, wherein the vaccine contains an adjuvant.

34. The vaccine or immunogenic composition according to claim 33, wherein the vaccine contains a plasmid vector and the adjuvant contains a cationic lipid containing a quatemary ammonium salt, or formula $$R_1OCH_2CH(OR_1)CH_2N^+(CH_3)_2(R_2)X$$

wherein R1 is a linear, saturated or unsaturated aliphatic radical having 12 to 18 carbon atoms, R2 is another aliphatic radical containing 2 or 3 carbon atoms, and X denotes a hydroxyl or amine group.

35. The vaccine or immunogenic composition according to claim 34, wherein the adjuvant contains DMRIE.

36. The vaccine or immunogenic composition according to claim 33, wherein the vaccine contains a plasmid vector and the adjuvant contains a polymer of acrylic or methacrylic acid, or a polymer of maleic anhydride and an alkenyl derivative.

37. The vaccine or immunogenic composition according to claim 33, wherein the adjuvant contains GM-CSF.

38. The vaccine or immunogenic composition according to claim 33, wherein it contains a vector which expresses GM-CSF in vivo.

39. The vaccine or immunogenic composition according to claim 35, wherein the DMRIE is combined with a neutral lipid.

40. The vaccine or immunogenic composition according to claim 39, wherein the DMRIE is combined with DOPE to form DMRIE-DOPE.

41. A vaccine against foot-and-mouth disease, comprising an effective amount of an antigen and a veterinarily acceptable vehicle excipient: wherein the antigen comprises empty capsids of foot and mouth disease virus, obtained by expression in vitro, in eukaryotic cells, of cDNA encoding the P1 region and 3C protease of foot-and-mouth virus, and heat stabilizing a non-naturally occurring sulphur-sulphur bond in the P1 region, wherein the P1 region has the formula X1 Gly X3 X4 Gly X6 Leu X8 X9 Ser X11 X12 Tyr Met (SEQ ID NO: 43)

X4 and X11 are Tyr, His or Phe; and

X3, X8 and X12 are Val, Met, Ile, Thr or Ala; and

X1 is His or Lys; and

X9 is Asp, Glu or Lys; and

X6 is Cys;

and Cys at X6 does not naturally occur in the P1 region, and the non-naturally occurring sulphur-sulphur bond is from X6 being a Cys.

* * * * *

SEQUENCE LISTING

```
<160> NUMBER OF SEQ ID NOS: 41

<210> SEQ ID NO 1
<211> LENGTH: 37
<212> TYPE: DNA
<213> ORGANISM: Artificial sequence
<220> FEATURE:
<223> OTHER INFORMATION: oligonucleotide JCA305 used in RT-PCR in
      example 3 to create fragment A

<400> SEQUENCE: 1
ttttgatatc atgggtgctg ggcagtccag cccagca                              37

<210> SEQ ID NO 2
<211> LENGTH: 21
<212> TYPE: DNA
<213> ORGANISM: Artificial sequence
<220> FEATURE:
<223> OTHER INFORMATION: oligonucleotide JCA306 used in RT-PCR in
      example 3 to create fragment A

<400> SEQUENCE: 2
ttcacgacga aagtactatc c                                               21

<210> SEQ ID NO 3
<211> LENGTH: 21
<212> TYPE: DNA
<213> ORGANISM: Artificial sequence
<220> FEATURE:
<223> OTHER INFORMATION: oligonucleotide JCA307 used in PCR in
      example 3 to create fragment B

<400> SEQUENCE: 3
ctgaaggacc ctactccggg c                                               21

<210> SEQ ID NO 4
<211> LENGTH: 37
```

```
<212> TYPE: DNA
<213> ORGANISM: Artificial sequence
<220> FEATURE:
<223> OTHER INFORMATION: oligonucleotide JCA308 used in PCR in
      example 3 to create fragment B

<400> SEQUENCE: 4
ttttagatct tcaaagcttt gttttgcgca tcacgtg                              37

<210> SEQ ID NO 5
<211> LENGTH: 37
<212> TYPE: DNA
<213> ORGANISM: Artificial sequence
<220> FEATURE:
<223> OTHER INFORMATION: oligonucleotide JCA309 used in PCR in
      example 4 to create fragment C

<400> SEQUENCE: 5
ttttgatatc atggggctg gacaatccag tccagcg                              37

<210> SEQ ID NO 6
<211> LENGTH: 21
<212> TYPE: DNA
<213> ORGANISM: Artificial sequence
<220> FEATURE:
<223> OTHER INFORMATION: oligonucleotide JCA310 used in PCR in
      example 4 to create fragment C

<400> SEQUENCE: 6
ttcacgacga aggtgctgtc c                                              21

<210> SEQ ID NO 7
<211> LENGTH: 18
<212> TYPE: DNA
<213> ORGANISM: Artificial sequence
<220> FEATURE:
<223> OTHER INFORMATION: oligonucleotide JCA311 used in PCR in
      example 4 to create fragment D

<400> SEQUENCE: 7 aaggaccta cgccggac                                                   18

<210> SEQ ID NO 8
<211> LENGTH: 34
<212> TYPE: DNA
<213> ORGANISM: Artificial sequence
<220> FEATURE:
<223> OTHER INFORMATION: oligonucleotide JCA312 used in PCR in
      example 4 to create fragment D

<400> SEQUENCE: 8
ttttagatct tcaaagcttg gttttgcgca tcac                                34

<210> SEQ ID NO 9
<211> LENGTH: 37
<212> TYPE: DNA
<213> ORGANISM: Artificial sequence
<220> FEATURE:
<223> OTHER INFORMATION: oligonucleotide JCA313 used in PCR in
      example 4 to create fragment E

<400> SEQUENCE: 9
ttttgatatc atgggagctg gcaatccag cccagcg                              37

<210> SEQ ID NO 10
<211> LENGTH: 23
<212> TYPE: DNA
```

<213> ORGANISM: Artificial sequence
<220> FEATURE:
<223> OTHER INFORMATION: oligonucleotide JCA314 used in PCR in
      example 4 to create fragment E

<400> SEQUENCE: 10
ttcacgacaa acgtgctgtc cag                                          23

<210> SEQ ID NO 11
<211> LENGTH: 21
<212> TYPE: DNA
<213> ORGANISM: Artificial sequence
<220> FEATURE:
<223> OTHER INFORMATION: oligonucleotide JCA315 used in PCR in
      example 4 to create fragment F

<400> SEQUENCE: 11
agagcaaccg caagctgaag g                                            21

<210> SEQ ID NO 12
<211> LENGTH: 34
<212> TYPE: DNA
<213> ORGANISM: Artificial sequence
<220> FEATURE:
<223> OTHER INFORMATION: oligonucleotide JCA316 used in PCR in
      example 4 to create fragment F

<400> SEQUENCE: 12
ttttagatct tcaaagcttg gttttgcgca ttac                              34

<210> SEQ ID NO 13
<211> LENGTH: 37
<212> TYPE: DNA
<213> ORGANISM: Artificial sequence
<220> FEATURE:
<223> OTHER INFORMATION: oligonucleotide JCA317 used in PCR in
      example 4 to create fragment G

<400> SEQUENCE: 13
ttttgatatc atgggggccg gcaatccag tccggcg                            37

<210> SEQ ID NO 14
<211> LENGTH: 31
<212> TYPE: DNA
<213> ORGANISM: Artificial sequence
<220> FEATURE:
<223> OTHER INFORMATION: oligonucleotide JCA318 used in PCR in
      example 4 to create fragment G

<400> SEQUENCE: 14
ttttctcgag gggggccggc acgtgaaaga g                                 31

<210> SEQ ID NO 15
<211> LENGTH: 31
<212> TYPE: DNA
<213> ORGANISM: Artificial sequence
<220> FEATURE:
<223> OTHER INFORMATION: oligonucleotide JCA319 used in PCR in
      example 4 to create fragment H

<400> SEQUENCE: 15
ttttctcgag ggaccggtga agaagcctgt c                                 31

<210> SEQ ID NO 16
<211> LENGTH: 37
<212> TYPE: DNA
<213> ORGANISM: Artificial sequence -continued

```
<220> FEATURE:
<223> OTHER INFORMATION: oligonucleotide JCA320 used in PCR in
      example 4 to create fragment H

<400> SEQUENCE: 16
ttttagatct tcagcggcgg aacagcgctt tgtcctc                              37

<210> SEQ ID NO 17
<211> LENGTH: 24
<212> TYPE: DNA
<213> ORGANISM: Artificial sequence
<220> FEATURE:
<223> OTHER INFORMATION: oligonucleotide JCA321 used in PCR in
      example 5 to create fragment I

<400> SEQUENCE: 17
tttgacctaa cgtcggagaa gaag                                           24

<210> SEQ ID NO 18
<211> LENGTH: 37
<212> TYPE: DNA
<213> ORGANISM: Artificial sequence
<220> FEATURE:
<223> OTHER INFORMATION: oligonucleotide JCA322 used in PCR in
      example 6 to amplify a fragment of about 3462 bp

<400> SEQUENCE: 18
ttttgaattc atgcagtcca gcccagcaac cggctcg                             37

<210> SEQ ID NO 19
<211> LENGTH: 44
<212> TYPE: DNA
<213> ORGANISM: Artificial sequence
<220> FEATURE:
<223> OTHER INFORMATION: oligonucleotide JCA323 used in PCR in
      example 6 to amplify a fragment of about 3462 bp

<400> SEQUENCE: 19
ttttgaattc ataaaaatca agctttgtt ttgcgcatca cgtg                      44

<210> SEQ ID NO 20
<211> LENGTH: 37
<212> TYPE: DNA
<213> ORGANISM: Artificial sequence
<220> FEATURE:
<223> OTHER INFORMATION: oligonucleotide JCA324 used in PCR in
      example 7 to amplify a fragment of about 3470 bp

<400> SEQUENCE: 20
ttttgaattc atgggggctg gacaatccag tccagcg                             37

<210> SEQ ID NO 21
<211> LENGTH: 41
<212> TYPE: DNA
<213> ORGANISM: Artificial sequence
<220> FEATURE:
<223> OTHER INFORMATION: oligonucleotide JCA325 used in PCR in
      example 7 to amplify a fragment of about 3470 bp

<400> SEQUENCE: 21
ttttgaattc ataaaaatca agcttggtt ttgcgcatca c                         41

<210> SEQ ID NO 22
<211> LENGTH: 37
<212> TYPE: DNA
<213> ORGANISM: Artificial sequence
<220> FEATURE:
```

<223> OTHER INFORMATION: oligonucleotide JCA326 used in PCR in
      example 7 to amplify a fragment of about 3460 bp

<400> SEQUENCE: 22
ttttgaattc atgggagctg ggcaatccag cccagcg                              37

<210> SEQ ID NO 23
<211> LENGTH: 41
<212> TYPE: DNA
<213> ORGANISM: Artificial sequence
<220> FEATURE:
<223> OTHER INFORMATION: oligonucleotide JCA327 used in PCR in
      example 7 to amplify a fragment of about 3460 bp

<400> SEQUENCE: 23
ttttgaattc ataaaaatca agcttggtt ttgcgcatta c                          41

<210> SEQ ID NO 24
<211> LENGTH: 37
<212> TYPE: DNA
<213> ORGANISM: Artificial sequence
<220> FEATURE:
<223> OTHER INFORMATION: oligonucleotide JCA328 used in PCR in
      example 7 to amplify a fragment of about 3550 bp

<400> SEQUENCE: 24
ttttgaattc atgggggccg ggcaatccag tccggcg                              37

<210> SEQ ID NO 25
<211> LENGTH: 44
<212> TYPE: DNA
<213> ORGANISM: Artificial sequence
<220> FEATURE:
<223> OTHER INFORMATION: oligonucleotide JCA329 used in PCR in
      example 7 to amplify a fragment of about 3550 bp

<400> SEQUENCE: 25
ttttgaattc ataaaaatca gcggcggaac agcgctttgt cctc                      44

<210> SEQ ID NO 26
<211> LENGTH: 27
<212> TYPE: DNA
<213> ORGANISM: Artificial sequence
<220> FEATURE:
<223> OTHER INFORMATION: oligonucleotide JCA330 used in PCR in
      example 15 to amplify a fragment of about 559 bp

<400> SEQUENCE: 26
tgagtccacc aggcacccga agacacc                                        27

<210> SEQ ID NO 27
<211> LENGTH: 27
<212> TYPE: DNA
<213> ORGANISM: Artificial sequence
<220> FEATURE:
<223> OTHER INFORMATION: oligonucleotide JCA331 used in PCR in
      example 15 to amplify a fragment of about 1020 bp (fragment M)

<400> SEQUENCE: 27
ggtgtcttcg ggtgcctggt ggactca                                        27

<210> SEQ ID NO 28
<211> LENGTH: 36
<212> TYPE: DNA
<213> ORGANISM: Artificial sequence
<220> FEATURE:
<223> OTHER INFORMATION: oligonucleotide JCA332 used in PCR in

```
                                            -continued
    example 15 to amplify a fragment of about 1020 bp (fragment M)

<400> SEQUENCE: 28
aaagtctttg ccggcgctag ccgacactaa caaggt                           36

<210> SEQ ID NO 29
<211> LENGTH: 27
<212> TYPE: DNA
<213> ORGANISM: Artificial sequence
<220> FEATURE:
<223> OTHER INFORMATION: oligonucleotide JCA333 used in PCR in
      example 16 to amplify a fragment of about 559 bp (fragment O)

<400> SEQUENCE: 29
cgagtcagtc aggcagccgt agacacc                                     27

<210> SEQ ID NO 30
<211> LENGTH: 27
<212> TYPE: DNA
<213> ORGANISM: Artificial sequence
<220> FEATURE:
<223> OTHER INFORMATION: oligonucleotide JCA334 used in PCR in
      example 16 to amplify a fragment of about 1147 bp (fragment P)

<400> SEQUENCE: 30
ggtgtctacg gctgcctgac tgactcg                                     27

<210> SEQ ID NO 31
<211> LENGTH: 36
<212> TYPE: DNA
<213> ORGANISM: Artificial sequence
<220> FEATURE:
<223> OTHER INFORMATION: oligonucleotide JCA335 used in PCR in
      example 16 to amplify a fragment of about 1147 bp (fragment P)

<400> SEQUENCE: 31
agacgtccgt gtgttggcgc ctctggatct gtgttt                           36

<210> SEQ ID NO 32
<211> LENGTH: 27
<212> TYPE: DNA
<213> ORGANISM: Artificial sequence
<220> FEATURE:
<223> OTHER INFORMATION: oligonucleotide JCA336 used in PCR in
      example 17 to amplify a fragment of about 559 bp (fragment R)

<400> SEQUENCE: 32
tgacttgacg aggcacccgt aaacacc                                     27

<210> SEQ ID NO 33
<211> LENGTH: 27
<212> TYPE: DNA
<213> ORGANISM: Artificial sequence
<220> FEATURE:
<223> OTHER INFORMATION: oligonucleotide JCA337 used in PCR in
      example 17 to amplify a fragment of about 681 bp (fragment S)

<400> SEQUENCE: 33
ggtgtttacg ggtgcctcgt caagtca                                     27

<210> SEQ ID NO 34
<211> LENGTH: 36
<212> TYPE: DNA
<213> ORGANISM: Artificial sequence
<220> FEATURE:
<223> OTHER INFORMATION: oligonucleotide JCA338 used in PCR in
      example 17 to amplify a fragment of about 681 bp (fragment S)
```

```
<400> SEQUENCE: 34
gtagtactgg gccaagccgg ccaagtaggt gtttga                              36

<210> SEQ ID NO 35
<211> LENGTH: 27
<212> TYPE: DNA
<213> ORGANISM: Artificial sequence
<220> FEATURE:
<223> OTHER INFORMATION: oligonucleotide JCA339 used in PCR in
      example 18 to amplify a fragment of about 559 bp (fragment U)

<400> SEQUENCE: 35
cgagtccacc aagcatccaa agacacc                                        27

<210> SEQ ID NO 36
<211> LENGTH: 27
<212> TYPE: DNA
<213> ORGANISM: Artificial sequence
<220> FEATURE:
<223> OTHER INFORMATION: oligonucleotide JCA340 used in PCR in
      example 18 to amplif a fragment of about 507 bp (fragment V)

<400> SEQUENCE: 36
ggtgtctttg gatgcttggt ggactcg                                        27

<210> SEQ ID NO 37
<211> LENGTH: 36
<212> TYPE: DNA
<213> ORGANISM: Artificial sequence
<220> FEATURE:
<223> OTHER INFORMATION: oligonucleotide JCA341 used in PCR in
      example 18 to amplify a fragment of about 507 bp (fragment V)

<400> SEQUENCE: 37
cccagggtag ttagtcctag gcgggttgta cacctt                              36

<210> SEQ ID NO 38
<211> LENGTH: 1147
<212> TYPE: PRT
<213> ORGANISM: Foot-and-mouth disease virus

<400> SEQUENCE: 38

Met Gly Ala Gly Gln Ser Ser Pro Ala Thr Gly Ser Gln Asn Gln Ser
  1               5                  10                  15

Gly Asn Thr Gly Ser Ile Ile Asn Asn Tyr Tyr Met Gln Gln Tyr Gln
             20                  25                  30

Asn Ser Met Ser Thr Gln Leu Gly Asp Asn Thr Ile Ser Gly Gly Ser
         35                  40                  45

Asn Glu Gly Ser Thr Asp Thr Thr Ser Thr His Thr Thr Asn Thr Gln
     50                  55                  60

Asn Asn Asp Trp Phe Ser Lys Leu Ala Ser Ser Ala Phe Thr Gly Leu
 65                  70                  75                  80

Phe Gly Ala Leu Leu Ala Asp Lys Lys Thr Glu Glu Thr Thr Leu Leu
                 85                  90                  95

Glu Asp Arg Ile Leu Thr Thr Arg Asn Gly His Thr Thr Ser Thr Thr
            100                 105                 110

Gln Ser Ser Val Gly Val Thr Tyr Gly Tyr Ser Thr Glu Glu Asp His
        115                 120                 125

Val Ala Gly Pro Asn Thr Ser Gly Leu Glu Thr Arg Val Val Gln Ala
    130                 135                 140
```

-continued

Glu Arg Phe Phe Lys Lys Phe Leu Phe Asp Trp Thr Thr Asp Lys Pro
145                 150                 155                 160

Phe Gly Tyr Leu Thr Lys Leu Glu Leu Pro Thr Asp His His Gly Val
            165                 170                 175

Phe Gly His Leu Val Asp Ser Tyr Ala Tyr Met Arg Asn Gly Trp Asp
        180                 185                 190

Val Glu Val Ser Ala Val Gly Asn Gln Phe Asn Gly Gly Cys Leu Leu
    195                 200                 205

Val Ala Met Val Pro Glu Trp Lys Ala Phe Asp Thr Arg Glu Lys Tyr
    210                 215                 220

Gln Leu Thr Leu Phe Pro His Gln Phe Ile Ser Pro Arg Thr Asn Met
225                 230                 235                 240

Thr Ala His Ile Thr Val Pro Tyr Leu Gly Val Asn Arg Tyr Asp Gln
            245                 250                 255

Tyr Lys Lys His Lys Pro Trp Thr Leu Val Val Met Val Leu Ser Pro
            260                 265                 270

Leu Thr Val Ser Asn Thr Ala Ala Pro Gln Ile Lys Val Tyr Ala Asn
        275                 280                 285

Ile Ala Pro Thr Tyr Val His Val Ala Gly Glu Leu Pro Ser Lys Glu
290                 295                 300

Gly Ile Phe Pro Val Ala Cys Ala Asp Gly Tyr Gly Gly Leu Val Thr
305                 310                 315                 320

Thr Asp Pro Lys Thr Ala Asp Pro Val Tyr Gly Lys Val Tyr Asn Pro
            325                 330                 335

Pro Lys Thr Asn Tyr Pro Gly Arg Phe Thr Asn Leu Leu Asp Val Ala
        340                 345                 350

Glu Ala Cys Pro Thr Phe Leu Arg Phe Asp Asp Gly Lys Pro Tyr Val
        355                 360                 365

Val Thr Arg Ala Asp Asp Thr Arg Leu Leu Ala Lys Phe Asp Val Ser
370                 375                 380

Leu Ala Ala Lys His Met Ser Asn Thr Tyr Leu Ser Gly Ile Ala Gln
385                 390                 395                 400

Tyr Tyr Thr Gln Tyr Ser Gly Thr Ile Asn Leu His Phe Met Phe Thr
            405                 410                 415

Gly Ser Thr Asp Ser Lys Ala Arg Tyr Met Val Ala Tyr Ile Pro Pro
        420                 425                 430

Gly Val Glu Thr Pro Pro Asp Thr Pro Glu Glu Ala Ala His Cys Ile
        435                 440                 445

His Ala Glu Trp Asp Thr Gly Leu Asn Ser Lys Phe Thr Phe Ser Ile
    450                 455                 460

Pro Tyr Val Ser Ala Ala Asp Tyr Ala Tyr Thr Ala Ser Asp Thr Ala
465                 470                 475                 480

Glu Thr Thr Asn Val Gln Gly Trp Val Cys Val Tyr Gln Ile Thr His
            485                 490                 495

Gly Lys Ala Glu Asn Asp Thr Leu Leu Val Ser Ala Ser Ala Gly Lys
        500                 505                 510

Asp Phe Glu Leu Arg Leu Pro Ile Asp Pro Arg Thr Gln Thr Thr Thr
        515                 520                 525

Thr Gly Glu Ser Ala Asp Pro Val Thr Thr Val Glu Asn Tyr Gly
        530                 535                 540

Gly Asp Thr Gln Val Gln Arg Arg His His Thr Asp Val Gly Phe Ile
545                 550                 555                 560

Met Asp Arg Phe Val Lys Ile Asn Ser Leu Ser Pro Thr His Val Ile

-continued

```
              565                 570                 575
Asp Leu Met Gln Thr His Lys His Gly Ile Val Gly Ala Leu Leu Arg
            580                 585                 590
Ala Ala Thr Tyr Tyr Phe Ser Asp Leu Glu Ile Val Val Arg His Asp
            595                 600                 605
Gly Asn Leu Thr Trp Val Pro Asn Gly Ala Pro Glu Ala Ala Leu Ser
            610                 615                 620
Asn Thr Ser Asn Pro Thr Ala Tyr Asn Lys Ala Pro Phe Thr Arg Leu
625                 630                 635                 640
Ala Leu Pro Tyr Thr Ala Pro His Arg Val Leu Ala Thr Val Tyr Asp
                645                 650                 655
Gly Thr Asn Lys Tyr Ser Ala Ser Asp Ser Arg Ser Gly Asp Leu Gly
            660                 665                 670
Ser Ile Ala Ala Arg Val Ala Thr Gln Leu Pro Ala Ser Phe Asn Tyr
            675                 680                 685
Gly Ala Ile Gln Ala Gln Ala Ile His Glu Leu Leu Val Arg Met Lys
            690                 695                 700
Arg Ala Glu Leu Tyr Cys Pro Arg Pro Leu Leu Ala Ile Lys Val Thr
705                 710                 715                 720
Ser Gln Asp Arg Tyr Lys Gln Lys Ile Ile Ala Pro Ala Lys Gln Leu
                725                 730                 735
Leu Asn Phe Asp Leu Leu Lys Leu Ala Gly Asp Val Glu Ser Asn Leu
            740                 745                 750
Gly Pro Phe Phe Phe Ala Asp Val Arg Ser Asn Phe Ser Lys Leu Val
            755                 760                 765
Asp Thr Ile Asn Gln Met Gln Glu Asp Met Ser Thr Lys His Gly Pro
770                 775                 780
Asp Phe Asn Arg Leu Val Ser Ala Phe Glu Glu Leu Ala Thr Gly Val
785                 790                 795                 800
Lys Ala Ile Arg Thr Gly Leu Asp Glu Ala Lys Pro Trp Tyr Lys Leu
                805                 810                 815
Ile Lys Leu Leu Ser Arg Leu Ser Cys Met Ala Ala Val Ala Ala Arg
            820                 825                 830
Ser Lys Asp Pro Val Leu Val Ala Ile Met Leu Ala Asp Thr Gly Leu
            835                 840                 845
Glu Arg Gln Lys Pro Leu Lys Val Arg Ala Lys Leu Pro Gln Gln Glu
            850                 855                 860
Gly Pro Tyr Ala Gly Pro Met Glu Arg Gln Lys Pro Leu Lys Val Lys
865                 870                 875                 880
Val Lys Ala Pro Val Val Lys Glu Gly Pro Tyr Glu Gly Pro Val Lys
                885                 890                 895
Lys Pro Val Ala Leu Lys Val Lys Ala Arg Asn Leu Ile Val Thr Glu
            900                 905                 910
Ser Gly Ala Pro Pro Thr Asp Leu Gln Lys Met Val Met Gly Asn Thr
            915                 920                 925
Lys Pro Val Glu Leu Asn Leu Asp Gly Lys Thr Val Ala Ile Cys Cys
            930                 935                 940
Ala Thr Gly Val Phe Gly Thr Ala Tyr Leu Val Pro Arg His Leu Phe
945                 950                 955                 960
Ala Glu Lys Tyr Asp Lys Ile Met Leu Asp Gly Arg Ala Met Thr Asp
                965                 970                 975
Ser Asp Tyr Arg Val Phe Glu Phe Glu Ile Lys Val Lys Arg Thr Gly
            980                 985                 990
```

His Ala Leu Arg Arg Gly Thr His Trp Leu His Arg Gly Asn Cys
        995                 1000                1005

Val Arg Asp Ile Thr Lys His Phe Arg Asp Thr Ala Arg Met Lys Lys
    1010                1015                1020

Gly Thr Pro Val Val Gly Val Val Asn Asn Ala Asp Val Gly Arg Leu
1025                1030                1035                1040

Ile Phe Ser Gly Glu Ala Leu Thr Tyr Lys Asp Ile Val Cys Met
            1045                1050                1055

Asp Gly Asp Thr Met Pro Gly Leu Phe Ala Tyr Lys Ala Ala Thr Arg
            1060                1065                1070

Ala Gly Tyr Cys Gly Gly Ala Val Leu Ala Lys Asp Gly Ala Asp Thr
        1075                1080                1085

Phe Ile Val Gly Thr His Ser Ala Gly Gly Asn Gly Val Gly Tyr Cys
    1090                1095                1100

Ser Cys Val Ser Arg Ser Met Leu Gln Lys Met Lys Ala His Val Asp
1105                1110                1115                1120

Pro Glu Pro His His Glu Gly Leu Ile Val Asp Thr Arg Asp Val Glu
            1125                1130                1135

Glu Arg Val His Val Met Arg Lys Thr Lys Leu
        1140                1145

<210> SEQ ID NO 39
<211> LENGTH: 3444
<212> TYPE: DNA
<213> ORGANISM: Foot-and-mouth disease virus

<400> SEQUENCE: 39
atgggtgctg ggcagtccag cccagcaacc ggctcgcaga accagtctgg caacactggc      60
agcataatta caactactac catgcagcaa taccagaact ctatgagcac acagcttggt     120
gacaatacca tcagtggagg ctccaacgag ggctccacgg acacaacttc aacacacaca     180
accaacaccc aaaacaacga ctggttttca aaacttgcca gttcggcttt taccggtctg     240
ttcggtgcac ttctcgccga caagaagacg aagagacta cgcttctgga agaccgcatc     300
ctcactaccc gcaacgggca caccacttcg accacccagt cgagtgtggg agtcacgtat     360
gggtactcca ctgaggaaga tcacgttgct gggcccaaca tcgggctt agagacgcgg     420 gtggtgcagg cagagagatt tttcaagaag tttctgtttg actggacaac ggacaaacct     480
tttggatact tgacaaaact ggagcttccc accgatcacc acggtgtctt cgggcacctg     540
gtggactcat atgcatatat gaggaacggc tgggatgttg aggtatctgc cgtcggcaac     600
cagttcaacg gcgggtgcct tctggtggcc atggtgccag agtggaaggc atttgacaca     660
cgtgaaaaat accagcttac ccttttccca caccagtttta ttagccccag aactaacatg     720
actgcccaca tcacggtacc gtatcttggt gtgaacaggt acgatcagta caagaaacac     780
aaaccttgga cactggttgt catggtacta tcacccctca cggtcagcaa cactgccgcc     840
ccacaaatca aggtctacgc caacattgcc caacctacg ttcacgtggc tggagagctt     900
ccctcgaaag aggggatttt cccagttgca tgcgcagacg gttacggagg actggtgaca     960
acagacccga aaacagctga ccctgtttac ggtaaggtgt ataaccccgcc aagaccaac    1020 taccccgggc gctttacaaa cctattggac gtggccgaag catgtccac cttttcttcgt   1080 ttcgacgatg ggaaaccgta cgtcgttacg cgggcagacg acaccgtct tttggccaag   1140 tttgatgtct cccttgccgc aaaacacatg tccaacacat acctatcagg gattgcacag   1200

-continued

```
tactacacac agtactctgg tactatcaac ctgcacttca tgttcacagg ctccactgac    1260
tcaaaagccc gctacatggt ggcttacatc ccgcctgggg tggagacgcc gccggacaca    1320
cctgaagaag ctgctcactg cattcacgct gagtgggaca caggactgaa ctccaaattc    1380
accttttcaa tcccttacgt gtctgccgcg gattacgcgt ataccgcatc tgatacggca    1440
gagacaacca atgtacaggg atgggtctgt gtttaccaaa ttacacacgg aaaggctgaa    1500
aatgacacct tgttagtgtc ggctagcgcc ggcaaagact ttgagttgcg cctcccaatt    1560 gaccccccgga cacaaaccac tactactggg gagtccgcag accctgtcac caccaccgtg    1620
gagaactacg gcggtgatac acaagtccag agacgtcacc acacggacgt cggcttcatt    1680
atggaccgat ttgtgaagat aaacagcctg agccccacac atgtcattga cctcatgcaa    1740
acccacaaac acgggatcgt gggtgcgtta ctgcgtgcag ccacgtacta cttctccgac    1800
ttggagattg ttgtgcggca cgatggtaat ctgacctggg tgcccaacgg tgcccccgag    1860
gcagccctgt caaacaccag caaccccact gcctacaaca aggcaccgtt cacgagactt    1920
gctctccctt acactgcgcc acaccgcgtg ttggcaactg tgtacgacgg acaaacaag    1980 tactccgcaa gcgattcgag atcaggcgac ctggggtcca tcgcggcgcg agtcgcgaca    2040
caacttcctg cttcctttaa ctacggtgca atccaggcac aggccatcca cgagcttctc    2100
gtgcgcatga acgggccga gctctactgt cccaggccac ttctagcaat aaaggtgact    2160
tcgcaagaca ggtacaagca aaagattatt gcgcccgcaa acagctgtt gaactttgac    2220 ctacttaagt tggcgggtga cgttgagtcc aaccttgggc ccttcttctt cgctgacgtt    2280 aggtcaaaact tttcgaagct ggtagacacc atcaatcaga tgcaggagga catgtccaca    2340
aaacacggac ccgacttttaa ccggttggtg tccgcttttg aggaattggc cactggggtt    2400
aaagctatca gaaccggtct cgatgaggcc aaaccctggt acaagctcat caagctccta    2460
agccgtctgt cgtgcatggc cgctgtggca gcacggtcca aggacccagt ccttgtggcc    2520
atcatgctgg ccgacaccgg tctcgagcgt cagaaacctc taaaagtgag agccaagctc    2580
ccacagcagg agggaccccta cgctggcccg atggagagac agaaaccgct gaaagtaaaa    2640
gtaaaagccc cggtcgttaa ggaaggacct tacgagggac cggtgaagaa gcctgtcgct    2700
ttgaaagtga agctaggaa cttgattgtc actgagagtg gtgccccacc gaccgacttg    2760
cagaagatgg tcatgggcaa cacaaagcct gttgagctta acctcgacgg aagacagta    2820 gccatctgct gtgctactgg agtgttcggc actgcttacc tcgtgcctcg tcaccttttc    2880
gcagagaagt atgacaagat tatgttggac ggcagagcca tgacagacag tgattacaga    2940
gtgtttgagt tcgagattaa agttaaaagg acaggacatg ctctcagacg cggcactcat    3000
tggttgcttc accgtgggaa ctgcgtgaga gacatcacga aacactttcg tgatacagca    3060
agaatgaaga aaggcacccc cgtcgttggt gttgtcaaca cgccgatgt tgggagactg    3120 attttctctg gtgaggccct tacctacaag gacattgtag tgtgcatgga tggagacacc    3180
atgcccggcc tctttgccta caaagccgcc accagggctg gctactgtgg aggagccgtt    3240
cttgccaagg acgggctga cacattcatc gtcggcactc actctgcagg tggcaatgga    3300
gttggatact gctcatgcgt ttccaggtcc atgcttcaaa agatgaaggc tcacgtcgac    3360
cctgaaccgc accacgaggg gttgattgtt gataccagag atgtggaaga gcgcgtccac    3420
gtgatgcgca aaacaaagct ttga                                           3444
```

```
<210> SEQ ID NO 40
<211> LENGTH: 28
```

-continued

```
<212> TYPE: DNA
<213> ORGANISM: Artificial sequence
<220> FEATURE:
<223> OTHER INFORMATION: oligonucleotide JCA342 used in PCR reaction on
      the genome of the vaccinia virus

<400> SEQUENCE: 40
ttttatcgat tcattgatag taccaaat                                        28

<210> SEQ ID NO 41
<211> LENGTH: 20
<212> TYPE: DNA
<213> ORGANISM: Artificial sequence
<220> FEATURE:
<223> OTHER INFORMATION: oligonucleotide JCA343 used in PCR reaction on
      the genome of the vaccinia virus

<400> SEQUENCE: 41
attctacagt tctaacatcc                                                 20
```